(12) United States Patent
Murphy et al.

(10) Patent No.: US 7,888,334 B2
(45) Date of Patent: Feb. 15, 2011

(54) MITOQUINONE DERIVATIVES USED AS MITOCHONDRIALLY TARGETED ANTIOXIDANTS

(75) Inventors: Michael Patrick Murphy, Cambridge (GB); Robin Smith, Dunedin (NZ)

(73) Assignee: Antipodean Pharmaceuticals, Inc., Menlo Park, CA (US)

( * ) Notice: Subject to any disclaimer, the term of this patent is extended or adjusted under 35 U.S.C. 154(b) by 938 days.

(21) Appl. No.: 10/568,654

(22) PCT Filed: Aug. 23, 2004

(86) PCT No.: PCT/NZ2004/000197

§ 371 (c)(1),
(2), (4) Date: Feb. 22, 2007

(87) PCT Pub. No.: WO2005/019233

PCT Pub. Date: Mar. 3, 2005

(65) Prior Publication Data

US 2007/0238709 A1    Oct. 11, 2007

(30) Foreign Application Priority Data

Aug. 22, 2003 (NZ) ..................... 527800
Oct. 23, 2003 (NZ) ..................... 529153
Jun. 14, 2004 (NZ) ..................... 533555

(51) Int. Cl.
*A61K 31/715* (2006.01)
*A61K 31/66* (2006.01)

(52) U.S. Cl. ........................... 514/58; 514/120; 514/121

(58) Field of Classification Search .................... 514/58, 514/120, 121
See application file for complete search history.

(56) References Cited

U.S. PATENT DOCUMENTS

| 3,532,667 | A | 10/1970 | Singh et al. ................... 524/99 |
| 6,133,322 | A | 10/2000 | Rustin et al. ................. 514/689 |
| 6,331,532 | B1 | 12/2001 | Murphy et al. |
| 6,673,908 | B1 | 1/2004 | Stanton, Jr. |
| 6,825,179 | B2 | 11/2004 | Nielsen et al. |
| 6,861,447 | B2 | 3/2005 | Moldenhauer et al. |
| 7,109,189 | B2 | 9/2006 | Murphy et al. |
| 7,179,928 | B2 | 2/2007 | Smith et al. |
| 7,232,809 | B2 | 6/2007 | Murphy et al. |
| 2002/0052342 | A1 | 5/2002 | Murphy et al. ................. 514/75 |
| 2003/0069208 | A1 | 4/2003 | Murphy et al. ................. 514/75 |
| 2004/0106579 | A1 | 6/2004 | Murphy et al. ................. 514/75 |
| 2006/0229278 | A1 | 10/2006 | Taylor et al. ................... 514/58 |
| 2007/0270381 | A1 | 11/2007 | Murphy et al. .............. 514/100 |
| 2008/0161267 | A1 | 7/2008 | Taylor et al. ................... 514/58 |
| 2008/0275005 | A1 | 11/2008 | Murphy et al. .............. 514/100 |
| 2009/0258841 | A1 | 10/2009 | Murphy et al. |

FOREIGN PATENT DOCUMENTS

| EP | 0 289 223 A1 | 11/1988 |
| EP | 5356036 B1 | 4/1993 |
| EP | 0535283 A1 | 11/1993 |
| EP | 549366 | 4/1998 |
| JP | 59-39855 | 3/1984 |
| JP | 03074395 A | 3/1991 |
| JP | 5-310763 | 11/1993 |
| JP | 7-223991 | 8/1995 |
| JP | 8-239340 | 9/1996 |
| JP | 2002104922 A | 4/2002 |
| JP | 2003520827 A | 7/2003 |
| JP | 09-278770 | 9/2006 |
| NZ | 513547 | 1/2003 |
| WO | 91/19815 A1 | 12/1991 |
| WO | 95/26973 A1 | 10/1995 |
| WO | 99/26582 A2 | 6/1999 |
| WO | 99/26954 A1 | 6/1999 |
| WO | 03/016323 | 2/2003 |
| WO | 03/065882 A2 | 8/2003 |
| WO | 2005/019232 A1 | 3/2005 |
| WO | 2005019233 A1 | 3/2005 |
| WO | 2009145982 A1 | 12/2009 |

OTHER PUBLICATIONS

Burns, R., et al., "Labeling Of Mitochondrial Proteins In Living Cells By The Thiol Probe Thiobutyltriphenylphosphonium Bromide," Arch .Biochem .Biophys., 339(1):33-9, Mar. 1, 1997.
Burns, R., et al., "Synthesis and Characterization Of Thiobutyltriphenylphosphonium Bromide, A Novel Thiol Reagent Targeted To The Mitochondrial Matrix," Arch. Biochem. Biophys., 322(1):60-8, Sep. 10, 1995.

(Continued)

*Primary Examiner*—Raymond J Henley, III
(74) *Attorney, Agent, or Firm*—Seed IP Law Group PLLC

(57) ABSTRACT

This invention relates to methods to screen for, identify, select and synthesise amphiphilic mitochondrially targeted antioxidant compounds, and compositions, dosage forms and methods reliant on said compounds. The exemplified compounds are all mitoquinone derivatives, being methoxyphenyl alkyl triphenylphosphonium or methoxy dioxocyclohexadiene alkyl triphenylphosphonium derivatives. The compounds, compositions, dosage forms and methods are useful in, for example, the treatment of diseases or conditions associated with oxidative stress.

40 Claims, 11 Drawing Sheets

OTHER PUBLICATIONS

Chen, L.B., "Mitochondrial Membrane Potential in Living Cells," Annual Review of Cell Biology, 4:155-181, Nov. 1988.

Coulter et al., Mitochondrially targeted antioxidants and thiol Reagents, Free Radical Biology & Medicine (2000), 28(10), 1547-1554.

Davey, G.P., et al., "Uptake and accumulation of 1-methyl-4-phenylpyridinium by rat liver mitochondria measured using an ion-selective electrode," Biochem J., 288(Pt 2): 439-443, Dec. 1, 1992.

Dean., W., et al. "Mitochondrial Nutrition, Aging and Cognition,"Smart Drug News (5)2, Aug. 1, 1996.

Ernster, L. et al., "The mode of action of lipid-soluble antioxidants in biological membranes: relationship between the effect of ubiquinol and vitamin E as inhibitors of lipid peroxidation in submitochondrial particles," BioFactors 3(4): 241-248 1992.

Everett, S., et al., "Scavenging Of Nitrogen Dioxide, Thiyl, and Sulfonyl Free Radicals By The Nutritional Antioxidant Beta-Carotene," *J. Biol. Chem.*, 271(8):3988-94, Feb. 23, 1996.

Goto, G., et al., "A Facile Synthesis of 1,4-Benzoquinones Having a Hydroxyalkyl Side Chain," Chem Pharm Bull (Tokyo), 33(10):4422-31, 1985.

Grisar, J. Martin et al., "Cardioselective ammonium, phosphonium, and sulfonium analogues of alpha-tocopherol and ascorbic acid that inhibit in vitro and ex vivo lipid peroxidation and scavenge superoxide radicals," 1: J Med Chem. 38(15):2880-6, Jul. 21, 1995.

James, A.M. et al.,"Antioxidant and prooxidant properties of mitochondrial coenzyme Q," Arch. Biochem. Biophys. 423, 47-56, 2004.

Jauslin, M. L., et al., "A cellular model for Friedreich Ataxia reveals small-molecule glutathione peroxidase mimetics as novel treatment strategy," Human Molecular Genetics, 11(24):3055-3063, 2002.

Jauslin, M., et al., "Mitochondria-Targeted Antioxidants Protect Friedreich Ataxia Fibroblasts From Endogenous Oxidative Stress More Effectively Than Untargeted Antioxidants," *FASEB J.*, 17(13):1972-4, Oct. 2003.

Kamo, N. et al., "Membrane potential measured with an electrods sensitive to tetraphenyl-phosphonium and relationship," J Membr. Biol, 49:105-121, 1979.

Keinan, E. et al., "Total synthesis of linear polyprenoids. II: Improved preparation of the aromatic nucleus of ubiquinone," J. Org. Chem. 52(17) 3872-3875, 1987.

Kelso, G., et al., "Prevention Of Mitochondrial Oxidative Damage Using Targeted Antioxidants," Ann. NY Acad. Sci., 959:263-74, Apr. 2002.

Koyama, Mayumi, et al., "Synthesis of Fluorine Analogs of Vitamin E. II. Synthesis of 2-(3-chloropropyl)-2,5,7,8-tetramethyl-6-chromano and its application for stereocontrolled Witting reaction and trifluromethyl ketones," Chemical and Pharmaceutical Bulletin, 36(8):2950-2954, 1988.

Masaki, N. et al., "Mitochondrial Damage as a Mechanism of Cell Injury in the Killing of Cultured Hepatocytes by tert-Butyl Hydroperoxide,"*Archives of Biochemistry and Biophysics*, 270(2): 672-680, May 1, 1989. (Abstract only).

Masaki, N., et al., "Intracellular Acidosis Protects Cultured Hepatocytes From The Toxic Consequences Of A Loss Of Mitochondrial Energization," Arch Biochem Biophys., 272(1):152-61, Jul. 1989. (Abstract only).

McKittrick et al., "Synthesis of the Yeast Antioxidant Benzofuran and Analogs," J. Chem. Soc. Perkin Trans, 1:709-712(721?), 1984.

Okamoto, K., et al., "Synthesis of quinones having carboxy- and hydroxy-alkyl side chains, and their effects on rat-liver lysosomal membrane," Chem Pharm Bull (Tokyo). Aug. 1982; 30(8):2797-819.

Rottenberg H., "The measurement of membrane potential and deltapH in cells, organelles, and vesicles," Methods Enzymol., 55:547-569, 1979.

Sakamoto, K. et al., "Role of the isoprenyl tail of ubiquinone in reaction with respiratory enzymes: studies with bovine heart mitochondrial complex I and *Escherichia coli* bo-type ubiquinol oxidase," Biochemistry 37(43), 15106-15113, Oct. 27, 1998.

Smith, Robin A.J., et al. "Targeting Coenzyme Q Derivatives to Mitochondria," Methods in Enzymology; Quinones and Quinone Enzymes, Part B, 382: 45-67, 2004.

Smith, Robin, A.J. et al., "Selective targeting of an antioxidant to mitochondria," *European Journal of Biochemistry*, 263:709-716, 1999.

Asin-Cayuela et al., "Fine-tuning the hydrophobicity of a mitochondria-targeted antioxidant," FEBS Letters 571:9-16, 2004.

Beg et al., "Spectroscopic studies of organophosphorus compounds," Pakistan J. of Scientific and Industrial Research 29(3):165-171, a abstract p. 1, 1986.

Kelso et al., "Selective Targeting of a Redox-active Ubiquinone to Mitochondria within Cells," Journal of Biological Chem. 276(7):4588-96, Feb. 16, 2001.

Littaru et al., "In vitro effect of different ubiquinones on the scavenging of biologically generated superoxide," Drugs Under Experimental and Clinical Research 11(8):529-532, Abstract Only, from CAPLUS, Accession No. 1986:2306, p. 1 of 1, 1985.

Murphy, Michael P., "Selective targeting of bioactive compounds to mitochondria," Trends in Biotechnology 15 (8):326-330, 1997.

Oliveira et al., "Oxidative stress in the pathogenesis of nonalcoholic fatty liver disease, in rats fed with a choline-deficient diet," J. Cell. Mol. Med. 6(3):399-406, 2002.

Saretzki et al., "MitoQ counteracts telomere shortening and elongates lifespan of fibroblasts under mild oxidative stress," Aging Cell 2:141-143, 2003.

Smith et al., "Delivery of bioactive molecules to mitochondria in vivo," PNAS 100(9):5407-5412, Apr. 29, 2003.

Videla et al., "Oxidative stress-related parameters in the liver of non-alcoholic fatty liver disease patients," Clinical Science 106:261-268, 2004.

MITOQUINONE DERIVATIVES USED AS MITOCHONDRIALLY TARGETED ANTIOXIDANTS

FIELD OF INVENTION

The invention relates to amphiphilic antioxidants having a lipophilic cationic group, their synthesis and physicochemical properties that favour their use as, for example, pharmaceuticals.

BACKGROUND

Oxidative stress contributes to a number of human degenerative diseases associated with ageing, such as Parkinson's disease, and Alzheimer's disease, as well as to Huntington's Chorea and Friedreich's Ataxia, and to non-specific damage that accumulates with aging. It also contributes to inflammation and ischaemic-reperfusion tissue injury in stroke and heart attack, and also during organ transplantation and surgery. To prevent the damage caused by oxidative stress a number of antioxidant therapies have been developed. However, most of these are not targeted within cells and are therefore less than optimally effective. Moreover, many such antioxidants have unfavourable physicochemical properties that limit for example, their bioavailability, and their ability to penetrate to the target organ to exert a therapeutic effect.

Mitochondria are intracellular organelles responsible for energy metabolism. Consequently, mitochondrial defects are damaging, particularly to neural and muscle tissues which have high energy demands. They are also the major source of the free radicals and reactive oxygen species that cause oxidative stress inside most cells. Therefore, the applicants believe delivering antioxidants selectively to mitochondria will be more effective than using non-targeted antioxidants. Accordingly, it is towards the provision of antioxidants which may be targeted to mitochondria that the present invention is directed.

Lipophilic cations may be accumulated in the mitochondrial matrix because of their positive charge (Rottenberg, 1979 *Methods Enzymol* 55, 547. Chen, 1988 *Ann Rev Cell Biol* 4, 155). Such ions are accumulated provided they are sufficiently lipophilic to screen the positive charge or delocalise it over a large surface area, also provided that there is no active efflux pathway and the cation is not metabolised or immediately toxic to a cell.

The focus of the invention is therefore on an approach by which it is possible to use the ability of mitochondria to concentrate specific lipophilic cations to take up linked antioxidants so as to target the antioxidant to the major source of free radicals and reactive oxygen species causing the oxidative stress.

Examples of antioxidant compounds that show good antioxidant activity yet exhibit poor bioavailability with respect to the target compartment in vivo include Coenzyme Q (CoQ) and Idebenone. Both of these compounds must be administered at very high dose rates to be efficacious, and therefore have low therapeutic efficacy when referenced to the dose rate administered.

We believe without wishing to be bound by any theory that for an antioxidant compound, activity in vitro or ex vivo (such as, for example, antioxidant activity or mitochondrial accumulation) is by no means the sole determinant of efficacy in vivo (such as, for example, therapeutic efficacy). Whilst it is true that to be useful as a mitochondrially targeted antioxidant compound of the present invention, an antioxidant compound must exhibit a suitable antioxidant activity in vitro or ex vivo, to be efficacious in vivo the mitochondrially targeted antioxidant compound must exhibit other desirable physicochemical properties, such as, for example, suitable bioavailability, localization or distribution within the target mitochondria, and/or suitable stability.

We believe without wishing to be bound by any theory that, at least in part by virtue of their physicochemical properties, such as, for example, their amphiphilicity and/or low partition coefficient, the mitochondrially targeted antioxidant compounds of the present invention exhibit advantageous antioxidant functionality, including bioavailability, and/or mitochondrial targeting and accumulation in vivo. Such compounds are thereby therapeutically efficacious at low dose rates in comparison to other antioxidant compounds.

In U.S. Pat. No. 6,331,532 by reference to exemplifications of compounds mitoquinol and mitoquinone (referred to collectively herein as mitoquinone/mitoquinol) there is disclosed the prospect of mitochondrial targeting of an antioxidant moiety reliant upon a lipophilic cation covalently coupled to the antioxidant moiety. The exemplified compound therein (despite generalisation of the bridge length), is the compound mitoquinone of the formula

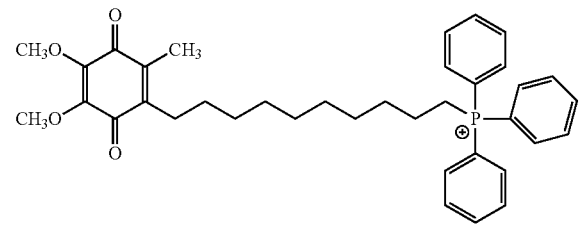

with a carbon bridge length of 10 (i.e. $C_{10}$ bridged). Its reduced form, mitoquinol, is also $C_{10}$ bridged.

Mitoquinone/mitoquinol, despite excellence in antioxidant activity and targeting and accumulation in mitochondria in vitro and in vivo, we have found to be somewhat unstable as the bromide salt.

We have also determined that mitoquinone (1)/mitoquinol has a moderately high partition coefficient (e.g. about 160 when assessed by an octanol:water partition system, see herein), that idebenone has a high partition coefficient of $3.1 \times 10^3$, and ubiquinone ($CoQ_{10}$) has a very high partition coefficient of $1.8 \times 10^{20}$.

We believe compounds of the general formula I

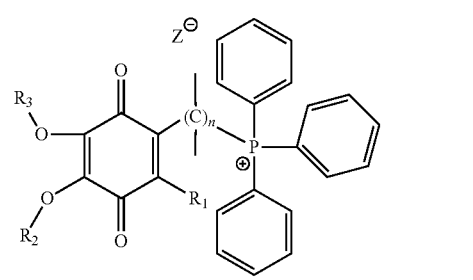

where the bridge length is less than about $C_{20}$ (for example less than about $C_{15}$, in other examples less than about $C_{10}$, and in other examples less than about $C_7$) surprisingly may provide in vivo antioxidant activity at or in the mitochondria many times beyond what would be expected from the in vitro or ex vivo studies of antioxidant activity, including mitochondrial targeting of antioxidant activity, and many times beyond that observed with, for example, derivatives of CoQ such as $CoQ_0$.

A lower partition coefficient is in our view desirable for particular applications, and may provide for greater bioavailability, particularly where administration is to be oral or parenteral and/or where there is targeting of the antioxidant compound to mitochondria in the tissues of internal organs (e.g. brain, heart or other organs). Conversely, we believe compounds which exhibit high partition coefficients may be less appropriate for delivery orally for the treatment of oxidative stress where there is a requirement for oral bioavailability, organ penetration, and for passage through a barrier such as that of the blood brain barrier.

In PCT/NZ02/00154 there is disclosed a process for manufacturing compounds of the general formula II

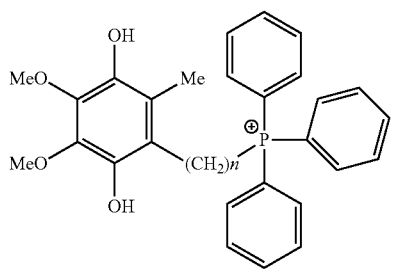

II

Such a procedure we have found is more suitable for chain lengths or for bridging groups greater than $C_6$ (i.e. where n>6) than it is for chain lengths or for bridging groups less than $C_6$ (i.e. where n<6).

The present invention recognises therefore an advantage in being able to prepare compounds of bridge length $C_6$ or less.

We have found on preparation of compounds of bridge length less than about $C_{10}$ that such compounds have distinct and desirable physicochemical properties from those taught within U.S. Pat. No. 633,152 and PCT/NZ02/00154.

Advantageously, examples of compounds of the present invention are crystalline and/or solid in form, which amongst other advantages renders them particularly suitable to formulation (e.g. by tableting or encapsuling) in pharmaceutical formulations for example in orally-administerable dosage forms. This results in novel mitochondrially targeted antioxidant compounds with desirable physicochemical properties particularly suited to therapeutic pharmaceutical use.

Other examples of compounds of the present invention may be in a form other than a crystalline and/or solid form, but may be amenable to formation of a solid form by admixture with other agents such as for example, carriers, excipients, complexation agents, or other additives and the like, such as, for example, cyclodextrins. Advantageously such agents are pharmaceutically acceptable.

We have also determined a desirability to offer examples of the amphiphilic mitochondrially targeted antioxidant compounds of the present invention with their positive charge in association with a suitable anion thereby to provide the compound as a general neutralised salt form, including but not limited to solid or crystalline products. In such salt forms however certain salt forming anions we have found to be best avoided as they exhibit reactivity against the antioxidant compound, for example, against the antioxidant moiety, the linking moiety, or the lipophilic cationic moiety, and/or may lead to cleavage at or of the antioxidant moiety. Other salt forming anions are considered pharmaceutically undesirable. For example, nitrate moieties are considered inappropriate generally by pharmaceutical companies as being pharmaceutically or environmentally unacceptable, whilst a hydrogen bromide frequently used in salt forming of such compounds we find to have nucleophilic properties that can lead to a reactivity against the antioxidant moiety, for example, a cleavage of a methyl group from the antioxidant moiety of the compound of general formula (II) herein, and/or some overall decrease in stability of the overall compound. For example, we have determined that the bromide salt of compound Mitoquinone is somewhat unstable.

We believe therefore that salt forms, including salt forms as a solid or crystalline form, of mitochondrially targeted antioxidants are best associated with an anion or like moiety that is not nucleophilic, or one which does not exhibit reactivity against any of the moieties comprising the antioxidant compound or complex. It is also preferable that the anion is pharmaceutically acceptable.

We further believe, without wishing to be bound by any theory, that at least in part by virtue of their physicochemical properties, the antioxidant compounds of the present invention are able to selectively target antioxidant activity to particular intracellular and/or intramitochondrial locations, for example so as to target particular reactive oxygen species, and/or particular sites of reactive oxygen species generation.

OBJECT OF THE INVENTION

Accordingly, it is an object of the present invention to provide amphiphilic mitochondrially targeted antioxidant compounds and compositions, dosage forms and methods reliant on said compounds, which are, for example, useful in the treatment of diseases or conditions associated with oxidative stress, in addition to providing methods to screen for, identify, or select such compounds, or to provide the public with a useful choice.

SUMMARY OF THE INVENTION

In a first aspect the present invention provides a mitochondrially targeted antioxidant compound having a lipophilic cationic moiety linked by a linking moiety to an antioxidant moiety wherein the nature of the linking moiety, the lipophilic cationic moiety and the antioxidant moiety is such that when targeted to mitochondria the antioxidant moiety is positioned at or proximal to a desired location within said mitochondria.

In one embodiment, said location is the outer mitochondrial membrane.

In another embodiment, said location is the intermembrane space of said mitochondria.

In another embodiment, said location is the inner mitochondrial membrane.

In another embodiment, said location is the mitochondrial matrix.

In a second aspect the present invention provides a mitochondrially targeted antioxidant compound having a lipophilic cationic moiety linked by a linking moiety to an antioxidant moiety wherein the nature of the linking moiety, the lipophilic cationic moiety and the antioxidant moiety is such that when located in or on or proximal to a mitochondrial membrane the distance from the lipophilic moiety to the antioxidant moiety is between about 5 and about 60 angstroms.

In some examples, the distance from the lipophilic moiety to the antioxidant moiety is between about 10 angstroms and about 50 angstroms, in other examples distance is between about 20 angstroms and 40 angstroms, and in further examples the distance is between about 25 angstroms and about 35 angstroms.

In a further embodiment, the linking moiety is a carbon chain having from about 1 to about 30 carbon atoms, for example, from about 2 to about 20 carbon atoms, from about 2 to about 15 carbon atoms, from about 3 to about 10 carbon atoms, or from about 3 to about 6 carbon atoms.

In one example, the compound is a compound of the formula

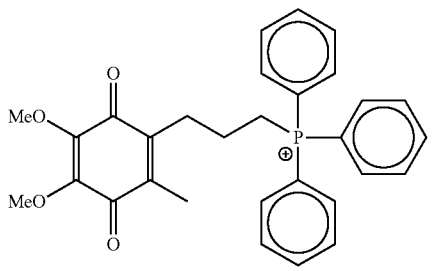

In another example, the compound is a compound of the formula

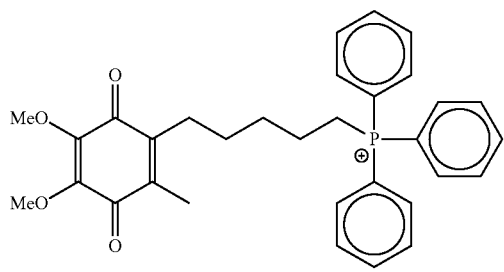

In another example, the compound is a compound of the formula

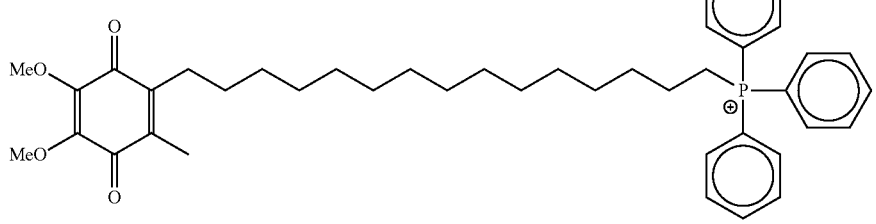

In another aspect the present invention provides a mitochondrially targeted antioxidant compound having a lipophilic cationic moiety linked by a linking moiety to an antioxidant moiety wherein the antioxidant moiety is capable of interacting with mitochondrial reductants.

In one embodiment, the antioxidant moiety is capable of repeated interaction with mitochondrial reductants thereby to achieve a recycling of antioxidant activity.

In a further aspect the present invention provides a mitochondrially targeted antioxidant compound having a lipophilic cationic moiety linked by a linking moiety to an antioxidant moiety wherein the antioxidant compound is a better substrate for reduction by components of the mitochondrial respiratory chain than it is a substrate for oxidation by components of the mitochondrial respiratory chain.

In a further aspect the present invention provides a method of preparing a mitochondrially targeted antioxidant compound which comprises selecting an antioxidant moiety, selecting a lipophilic cation, selecting a linking moiety capable of linking the antioxidant moiety to the lipophilic cation, wherein the linking moiety, the lipophilic moiety and/or the antioxidant moiety is selected so that when targeted to mitochondria the antioxidant moiety is positioned at or proximal to a desired location within said mitochondria.

In one embodiment, said location is the outer mitochondrial membrane.

In another embodiment, said location is the intermembrane space of said mitochondria.

In another embodiment, said location is the inner mitochondrial membrane.

In another embodiment, said location is the mitochondrial matrix.

In a further aspect the present invention provides a method of positioning the antioxidant moiety of a mitochondrially targeted antioxidant compound having a lipophilic cationic moiety linked by a linking moiety to an antioxidant moiety in a desired location in or on or proximal to a mitochondrial membrane, which involves selecting the linking moiety, the lipophilic moiety and/or the antioxidant moiety so that when targeted to mitochondria the antioxidant moiety is positioned at or proximal to said desired location within said mitochondria, and contacting said mitochondria with said antioxidant compound.

In one embodiment the linking moiety, the lipophilic moiety and/or the antioxidant moiety is such that when positioned in or on or proximal to a mitochondrial membrane the distance from the lipophilic moiety to the antioxidant moiety is between about 5 and about 60 angstroms.

In a further aspect the present invention provides a method of targeting a desired location of the antioxidant moiety of a mitochondrially targeted antioxidant compound having a lipophilic cationic moiety linked by a linking moiety to an antioxidant moiety, which involves selecting a particular chain length (or other relevant property) of the linking moiety which will position the antioxidant moiety to the desired location within the mitochondria, and bringing said antioxidant compound into contact with said mitochondria.

In a further aspect the present invention provides a method of screening for an amphiphilic antioxidant compound, said method comprising or including administering said compound to a mitochondrial preparation, observing or determining mitochondrial uptake of the compound in the presence of a mitochondrial membrane potential, observing and/or determining release of the compound in the absence of a mitochondrial membrane potential, wherein substantially incomplete release of said compound is indicative of efficacy.

In one embodiment uptake and release of said compound is observed and/or determined by methods as herein disclosed.

In one example said compound has uptake and release characteristic of that of Mitoquinone-C10.

In a further example said compound has uptake and release so as to have more that characteristic of FIG. 3C as opposed to that characteristic of FIG. 3A.

In a yet further aspect the present invention provides a method of screening for an amphiphilic antioxidant compound, said method comprising or including administering said compound to a mitochondrial preparation, observing and/or determining mitochondrial uptake of the compound in the presence of a mitochondrial membrane potential, observing and/or determining release of the compound in the absence of a mitochondrial membrane potential, wherein substantially complete release of said compound is indicative of efficacy.

In a further aspect the present invention provides a method of screening for an amphiphilic antioxidant compound, said method comprising or including administering said compound to a mitochondrial preparation, observing and/or determining mitochondrial uptake of the compound in the absence of a mitochondrial membrane potential, wherein at least partial uptake of said compound is indicative of efficacy.

In one embodiment, said method comprises one or more additional steps of observing and/or determining uptake of the compound in the presence of a mitochondrial membrane potential, and/or observing and/or determining release of the compound in the absence of a mitochondrial membrane potential, wherein substantially incomplete release of said compound is indicative of efficacy.

In one embodiment uptake and release of said compound is observed and/or determined by methods as herein disclosed.

In one example said compound has uptake and release characteristic of that of Mitoquinone-C15.

In a further example said compound has uptake and release so as to have more that characteristic of FIG. 3D as opposed to that characteristic of FIG. 3A.

In a yet further aspect the present invention provides a method of screening for an amphiphilic antioxidant compound, said method comprising or including administering said compound to a mitochondrial preparation, observing and/or determining mitochondrial uptake of the compound in the presence of a mitochondrial membrane potential, observing and/or determining release of the compound in the absence of a mitochondrial membrane potential, wherein complete release of said compound is indicative of efficacy.

In yet a further aspect the present invention provides a method of screening for an amphiphilic antioxidant compound, said method comprising or including administering said compound to a mitochondrial preparation, observing and/or determining mitochondrial uptake of the compound in the presence of a mitochondrial membrane potential, wherein at substantially no uptake of said compound is indicative of efficacy.

In one embodiment, said method comprises one or more additional steps of observing and/or determining uptake of the compound in the presence of a mitochondrial membrane potential, and/or observing and/or determining release of the compound in the absence of a mitochondrial membrane potential, wherein substantially complete release of said compound is indicative of efficacy.

In one embodiment uptake and release of said compound is observed and/or determined by methods as herein disclosed.

In one example said compound has uptake and release characteristic of that of Mitoquinone-C3.

In a further example said compound has uptake and release so as to have more that characteristic of FIG. 3A as opposed to that characteristic of FIG. 3D.

In a further aspect the present invention provides a method of reducing oxidative stress in a cell which comprises positioning in or on the outer mitochondrial membrane and/or in the intermembrane space and/or in or on the inner mitochondrial membrane and/or in the matrix an antioxidant moiety of a compound comprising a lipophilic cationic moiety linked to said antioxidant moiety.

In a further aspect the present invention provides a method of therapy or prophylaxis of a patient who would benefit from reduced oxidative stress which comprises or includes the step of administering to said patient a mitochondrially targeted antioxidant compound comprising a lipophilic cationic moiety linked by a linking moiety to an antioxidant moiety thereby to position in or on the outer mitochondrial membrane and/or in the intermembrane space and/or in or on the inner mitochondrial membrane and/or in the matrix said antioxidant moiety of said compound.

In another aspect, the invention provides a mitochondrially targeted antioxidant compound which comprises a lipophilic cation linked by a linking moiety to an antioxidant moiety, wherein the compound is crystalline or solid, and/or the compound has a partition coefficient (octanol:water) less than about 20, and the compound is a salt form in which the anion is non nucleophilic or exhibits no reactivity against the antioxidant moiety, the linking moiety, or the cationic moiety, and/or the compound is in a salt form where the salt is acceptable for pharmaceutical preparation.

Preferably, an acceptable salt form is that of the methanesulfonate.

Preferably, the lipophilic cation (preferably unsubstituted) is the triphenylphosphonium cation.

Preferably, the antioxidant moiety is a quinone or a quinol.

In a further aspect the present invention consists in a mitochondrially targeted antioxidant compound of the general formula I

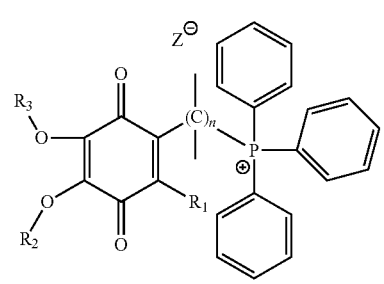

wherein $R_1$, $R_2$, and $R_3$, which can be the same or different, are selected from $C_1$ to $C_5$ alkyl (optionally substituted) moieties or H, and wherein n is an integer from about 2 to about 20, and wherein Z is an anion, and wherein the compound is crystalline or solid, and/or the compound has a partition coefficient (octanol:water) less than about 20, and the compound is a salt form in which the anion is non nucleophilic or exhibits no reactivity against the antioxidant moiety, the linking moiety, or the cationic moiety, and/or the compound is in a salt form where the salt is acceptable for pharmaceutical preparation.

Preferably, an acceptable salt form is that of the methanesulfonate.

Preferably, the lipophilic cation (preferably unsubstituted) is the triphenylphosphonium cation.

Preferably, the antioxidant moiety is a quinone or a quinol.

Preferably each C of the (C)n bridge is saturated.

In a further aspect, the present invention consists in a dosage unit suitable for oral administration comprising as an active ingredient a compound in accordance with the present invention, the compound being of or being formulated as a crystalline form and/or non-liquid form.

Preferably said compound is in the form of a salt.

Preferably said compound has a partition coefficient less than about 15.

In a further aspect, the invention provides a mitochondrially targeted antioxidant compound of the formula (2)

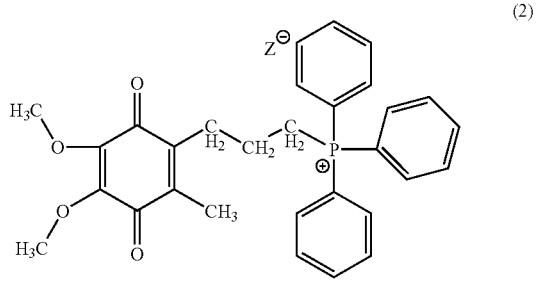

(2)

wherein Z is an anion that is not nucleophilic and/or does not exhibit reactivity against the antioxidant moiety, the cationic moiety and/or the linking moiety.

Preferably, Z is a pharmaceutically acceptable anion.

More preferably, Z is an alkyl or aryl sulfonate.

Preferably said compound is in the form of a salt.

Preferably said compound has a partition coefficient (octanol:water) less than about 20, more preferably less than about 15.

More preferably, the mitochondrially targeted antioxidant has the formula (A)

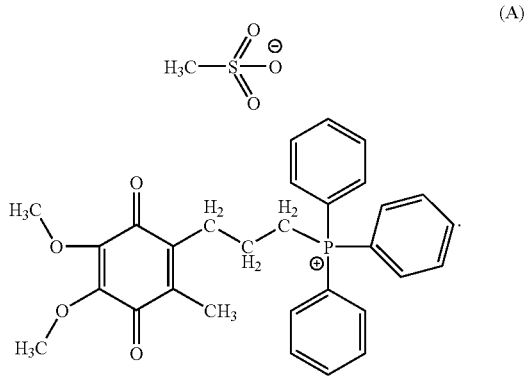

(A)

In a further aspect, the present invention provides a pharmaceutical composition suitable for treatment of a patient who would benefit from reduced oxidative stress or reduced symptoms of ageing which comprises or includes an effective amount of a mitochondrially targeted antioxidant compound of the present invention in combination with one or more pharmaceutically acceptable carriers or diluents.

In one embodiment the mitochondrially targeted antioxidant compound is a compound of formula I.

In another embodiment, the mitochondrially targeted antioxidant compound is compound (A).

In a further aspect, the invention provides a method of reducing oxidative stress in a cell which comprises the step of contacting said cell with a mitochondrially targeted antioxidant compound of the present invention.

In one embodiment the mitochondrially targeted antioxidant is a compound of formula I.

In another embodiment, the mitochondrially targeted antioxidant compound is compound (A).

In still a further aspect, the invention provides a method of therapy or prophylaxis of a patient who would benefit from reduced oxidative stress which comprises or includes the step of administering to said patient a mitochondrially targeted antioxidant compound of the present invention.

In one embodiment the mitochondrially targeted antioxidant is a compound of formula I.

In another embodiment, the mitochondrially targeted antioxidant compound is compound (A).

In a further aspect the invention provides a pharmaceutical composition suitable for the treatment of a patient who would benefit from reduced oxidative stress or reduced symptoms of ageing, which comprises an effective amount of a mitochondrially targeted antioxidant compound comprising a lipophilic cation linked by a linking moiety to an antioxidant moiety in combination with one or more pharmaceutically acceptable carriers or diluents, and wherein the compound is crystalline or solid, and/or the compound has a partition coefficient (octanol:water) less than about 20, and the compound is a salt form in which the anion is non nucleophilic or exhibits no reactivity against the antioxidant moiety, the linking moiety, or the cationic moiety, and/or the compound is in a salt form where the salt is acceptable for pharmaceutical preparation.

Preferably, an acceptable salt form is that of the methanesulfonate.

Preferably, the lipophilic cation (preferably unsubstituted) is the triphenylphosphonium cation.

Preferably, the antioxidant moiety is a quinone or a quinol.

In one embodiment the mitochondrially targeted antioxidant is a compound of formula I.

In one example the mitochondrially targeted antioxidant is compound (A).

In another aspect the invention provides a method of therapy or prophylaxis of a patient who would benefit from reduced oxidative stress or reduced symptoms of ageing which comprises the step of administering to the patient, a mitochondrially targeted antioxidant compound comprising a liphohilic cation linked by a linking moiety to an antioxidant moiety, and wherein the compound is crystalline or solid, and/or the compound has a partition coefficient (octanol:water) less than about 20, and the compound is a salt form in which the anion is non nucleophilic or exhibits no reactivity against the antioxidant moiety, the linking moiety, or the cationic moiety, and/or the compound is in a salt form where the salt is acceptable for pharmaceutical preparation.

Preferably, an acceptable salt form is that of the methanesulfonate.

Preferably, the lipophilic cation (preferably unsubstituted) is the triphenylphosphonium cation.

Preferably, the antioxidant moiety is a quinone or a quinol.

In one embodiment the mitochondrially targeted antioxidant is a compound of formula I.

In one example the mitochondrially targeted antioxidant is compound (A).

In another aspect the invention provides a method of therapy or prophylaxis of a patient who would benefit from reduced oxidative stress, or reduced symptoms of ageing, which comprises the step of administering to the patient a mitochondrially targeted antioxidant compound of the present invention.

In another aspect the invention provides a method of reducing oxidative stress in a cell, which comprises the step of administering to the cell a mitochondrially targeted antioxidant compound comprising a lipophilic cation linked by a linking moiety to an antioxidant moiety, wherein the compound is crystalline or solid, and/or the compound has a partition coefficient (octanol:water) less than about 20, and the compound is a salt form in which the anion is non nucleophilic or exhibits no reactivity against the antioxidant moiety, the linking moiety, or the cationic moiety, and/or the compound is in a salt form where the salt is acceptable for pharmaceutical preparation.

Preferably, an acceptable salt form is that of the methanesulfonate.

Preferably, the lipophilic cation (preferably unsubstituted) is the triphenylphosphonium cation.

Preferably, the antioxidant moiety is a quinone or a quinol.

In one embodiment the mitochondrially targeted antioxidant is a compound of formula I.

In one example the mitochondrially targeted antioxidant is compound (A).

In another aspect the invention provides a method of reducing oxidative stress in a cell, which comprises the step of administering to the cell a mitochondrially targeted antioxidant of the present invention.

Preferably, an acceptable salt form is that of the methanesulfonate.

Preferably, the lipophilic cation (preferably unsubstituted) is the triphenylphosphonium cation.

Preferably, the antioxidant moiety is a quinone or a quinol.

In one embodiment the mitochondrially targeted antioxidant is a compound of formula I.

In one example the mitochondrially targeted antioxidant is compound (A).

In another aspect the invention provides the use of a mitochondrially targeted antioxidant compound comprising a lipophilic cation linked by a linking moiety to an antioxidant moiety in the preparation or manufacture (with or without other material or materials) of a medicament, dosage unit, or pharmaceutical composition effective for use in the reduction of oxidative stress in a patient, wherein the compound is crystalline or solid, and/or the compound has a partition coefficient (octanol:water) less than about 20, and the compound is a salt form in which the anion is non nucleophilic or exhibits no reactivity against the antioxidant moiety, the linking moiety, or the cationic moiety, and/or the compound is in a salt form where the salt is acceptable for pharmaceutical preparation.

Preferably, an acceptable salt form is that of the methanesulfonate.

Preferably, the lipophilic cation (preferably unsubstituted) is the triphenylphosphonium cation.

Preferably, the antioxidant moiety is a quinone or a quinol.

In one embodiment the mitochondrially targeted antioxidant is a compound of formula I.

In one example the mitochondrially targeted antioxidant is compound (A).

In another aspect the invention provides the use of a compound as previously described in the preparation or manufacture with other material or materials of a medicament, dosage unit, or pharmaceutical composition effective for use in for the reduction of oxidative stress in a patient.

In another aspect the invention provides the use of a mitochondrially targeted antioxidant compound comprising a lipophilic cation linked by a liking moiety to an antioxidant in the preparation or manufacture (with or without other material or materials) of a medicament, dosage unit, or pharmaceutical composition effective for use in moiety for the reduction of symptoms of aging in a patient, wherein the compound is crystalline or solid, and/or the compound has a partition coefficient (octanol:water) less than about 20, and the compound is a salt form in which the anion is non nucleophilic or exhibits no reactivity against the antioxidant moiety, the linking moiety, or the cationic moiety, and/or the compound is in a salt form where the salt is acceptable for pharmaceutical preparation.

Preferably, an acceptable salt form is that of the methanesulfonate.

Preferably, the lipophilic cation (preferably unsubstituted) is the triphenylphosphonium cation.

Preferably, the antioxidant moiety is a quinone or a quinol.

In one embodiment the mitochondrially targeted antioxidant is a compound of formula I.

In one example the mitochondrially targeted antioxidant is compound (A).

In another aspect the invention provides the use of a compound as previously described in the preparation or manufacture with other material or materials of a medicament, dosage unit, or pharmaceutical composition effective for use for the reduction of symptoms of aging in a patient.

In another aspect the invention provides the use of a mitochondrially targeted antioxidant compound comprising a lipophilic cation linked by a linking moiety to an antioxidant moiety in the preparation or manufacture (with or without other material or materials) of a composition effective for use for the reduction of oxidative stress in a cell, wherein the compound is crystalline or solid, and/or the compound has a partition coefficient (octanol:water) less than about 20, and the compound is a salt form in which the anion is non nucleophilic or exhibits no reactivity against the antioxidant moiety, the lining moiety, or the cationic moiety, and/or the compound is in a salt form where the salt is acceptable for pharmaceutical preparation.

Preferably, an acceptable salt form is that of the methanesulfonate.

Preferably, the lipophilic cation (preferably unsubstituted) is the triphenylphosphonium cation.

Preferably, the antioxidant moiety is a quinone or a quinol.

In one embodiment the mitochondrially targeted antioxidant is a compound of formula I.

In one example the mitochondrially targeted antioxidant is compound (A).

In another aspect the invention provides a composition comprising or including a compound of the general formula I

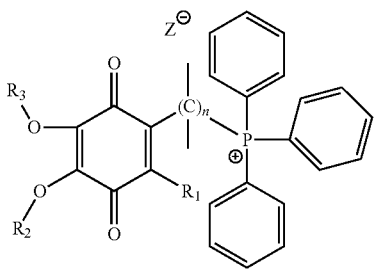

wherein $R_1$, $R_2$, and $R_3$, which can be the same or different, are selected from $C_1$ to $C_5$ alkyl (optionally substituted) moieties or H, and wherein n is an integer from about 2 to about 20, and wherein Z is an anion, and wherein the compound is crystalline in form and has a partition coefficient as herein defined less than about 20, and/or the compound is crystalline in form.

In another aspect the present invention provides a dosage unit comprising a mitochondrially targeted antioxidant compound, wherein
  the compound is crystalline or solid, and/or
  the compound has a partition coefficient (octanol:water) less than about 20, and/or
  the compound is a salt form in which the anion exhibits no reactivity against the antioxidant moiety, the linking moiety, or the cationic moiety and/or the compound is in a salt form where the salt is acceptable for pharmaceutical preparation, and/or
  the compound is a salt form in which the anion is non nucleophilic, and wherein the unit can be a capsule such as a gelatinized capsule, a tablet, or any other orally-administerable dosage unit.

Preferably an effective amount is present in any such dosage unit such effective amount being related to the dosage regime for the taking of such dosage units for any of the indications herein described.

In another aspect the invention provides the use of a compound as previously described in the preparation or manufacture with other material or materials of a medicament, dosage unit, or pharmaceutical composition effective for use in the reduction of oxidative stress in a cell.

In yet another aspect the present invention consists in a method of synthesis of a compound with a moiety or the moiety of the formula I

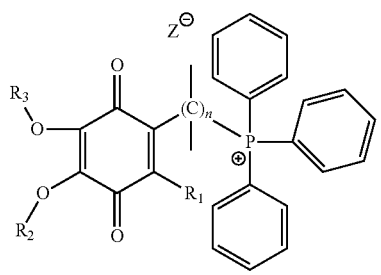

(and/or its quinone form) wherein R1, R2, and R3, which can be the same or different, are selected from $C_1$ to $C_5$ alkyl (optionally substituted) moieties, and wherein n is an integer from about 2 to about 20, and wherein Z is an anion, and the compound is a salt form in which the anion is non nucleophilic or exhibits no reactivity against the antioxidant moiety, the linking moiety, or the cationic moiety, and/or the compound is in a salt form where the salt is acceptable for pharmaceutical preparation.

Preferably each C of the (C)n bridge is saturated.

Preferably the compound is solid and/or crystalline.

Preferably the compound has a partition coefficient (octanol:water) less than about 20.

Preferably the formation of the compound from triphenylphosphonium does not involve reaction solvent.

In yet another aspect the present invention consists in a method of synthesis of a compound with a moiety or the moiety of the formula I

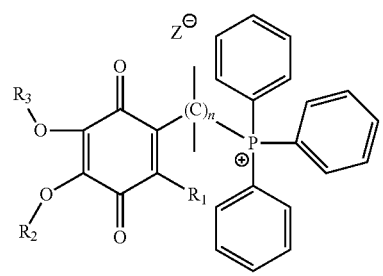

(and/or its quinone form) wherein $R_1$, $R_2$, and $R_3$, which can be the same or different, are selected from $C_1$ to $C_5$ alkyl (optionally substituted) moieties, and wherein n is an integer from about 2 to about 20, and wherein each C of the (C)n bridge is saturated, and wherein Z is an anion, which comprises or includes the reaction of a compound of the formula IV

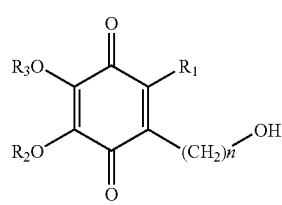

(and/or its quinol form) in the presence of $Ph_3PHX$ and $Ph_3P$, where X is a halogen atom.

Preferably X is preferably bromine, iodine or chlorine (most preferably bromine).

Preferably n is from 2 to about 5.

More preferably n is 3.

Preferably the reaction is maintained as a temperature below which significant amounts of $R_2PPh_3$, or $R_3PPh_3$, are not formed by ether cleavage, eg; the mixture is preferably kept below 80° C.

Preferably the formation of the compound from triphenylphosphonium does not involve reaction solvent.

In yet another aspect the present invention consists in a method of synthesis of a compound with a moiety or the moiety of the formula (2)

(2)

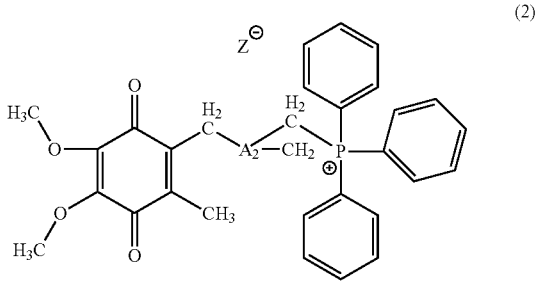

(and/or its quinol form), wherein Z is an anion, which comprises or includes the reaction of a compound of the formula (3)

(3)

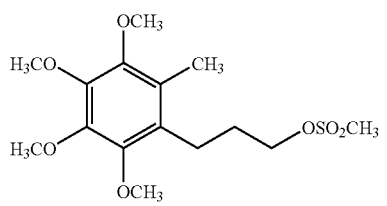

in the presence of Ph$_3$P and X, where X comprises or includes a halogen atom.

Preferably X comprises or includes bromine, iodine or chlorine (most preferably iodine).

Preferably the reaction is maintained as a temperature below which significant amounts of MePPh$_3$ are not formed by ether cleavage, eg; the mixture is preferably kept below 80° C.

Preferably the formation of the compound from triphenylphosphonium does not involve reaction solvent.

In a further aspect the present invention consists in a method of synthesis of a compound with a moiety or the moiety of the formula I

I

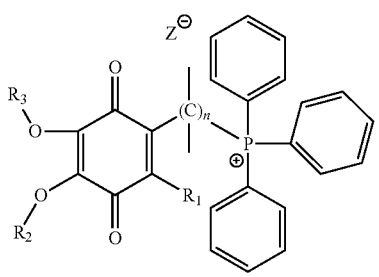

(and/or its quinone form) wherein R$_1$, R$_2$, and R$_3$, which can be the same or different, are selected from C$_1$ to C$_5$ alkyl (optionally substituted) moieties, and wherein n is an integer from about 2 to about 15, and wherein each C of the (C)n bridge is saturated, said method substantially as herein described.

Preferably, said method is reliant upon the method depicted in Scheme 1 herein.

More preferably, said method is reliant upon the method depicted in Scheme 1 herein in conjunction with that depicted in Scheme 3 herein.

Preferably the formation of the compound from triphenylphosphonium does not involve reaction solvent.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Throughout this specification the term "quinone", whether used alone or prefixed with another term to describe the oxidized form of a compound, will be understood to include within its scope the reduced form of that compound, that is, the quinol form. Similarly, reference to a quinone, by structural depiction for example, also includes within its scope the quinol form.

Throughout this specification the term "quinol", whether used alone or prefixed with another term to describe the reduced form of a compound, will be understood to include within its scope the oxidised form of that compound, that is, the quinone form. Similarly, reference to a quinol, by structural depiction for example, also includes within its scope the quinone form.

As used herein the term "and/or" includes both "and" and "or" as options.

As used herein, the term "partition coefficient" and "partition coefficient (octanol:water)" refer to the octan-1-ol/phosphate buffered saline partition coefficient determined at 25° C. or 37° C. (see Kelso, G. F., Porteous, C. M., Coulter, C. V., Hughes, G. Porteous, W. K., Ledgerwood, E. C., Smith, R. A. J. and Murphy, M. P. 2001 J Biol Chem 276 4588. Smith, R. A. J., Porteous, C. M., Coulter, C. V. and Murphy, M. P. 1999 Eu. J Biochem 263, 709. Smith, R. A. J., Porteous, C. M., Gane, A. M. and Murphy, M. P. 2003 Proc Nat Acad Sci 100, 5407.), or the octanol/water partition coefficient calculated using Advanced Chemistry Development (ACD) Software Solaris V4.67 as described in Jauslin, M. L., Wirth, T., Meier, T., and Schoumacher, F., 2002, Hum Mol Genet 11, 3055.

As used herein, the phrase "acceptable for pharmaceutical preparation" includes within its meaning not only an acceptability with regard to pharmaceutical administration, but also in respect of formulation for, for example, acceptable stability, shelf life, hygroscopicity, preparation and the like.

As used herein a "non-reactive anion" is an anion which exhibits no reactivity against the antioxidant moiety, the lipophilic cation, or the linking moiety. For example, if one such moiety of the compound comprises a target of nucleophilic attack, the anion is non-nucleophilic.

Although broadly as defined above, the invention is not limited thereto but also consists of embodiments of which the following description provides examples.

In particular, a better understanding of the invention will be gained with reference to the accompanying drawings.

DETAILED DESCRIPTION OF THE INVENTION

Figure 1:
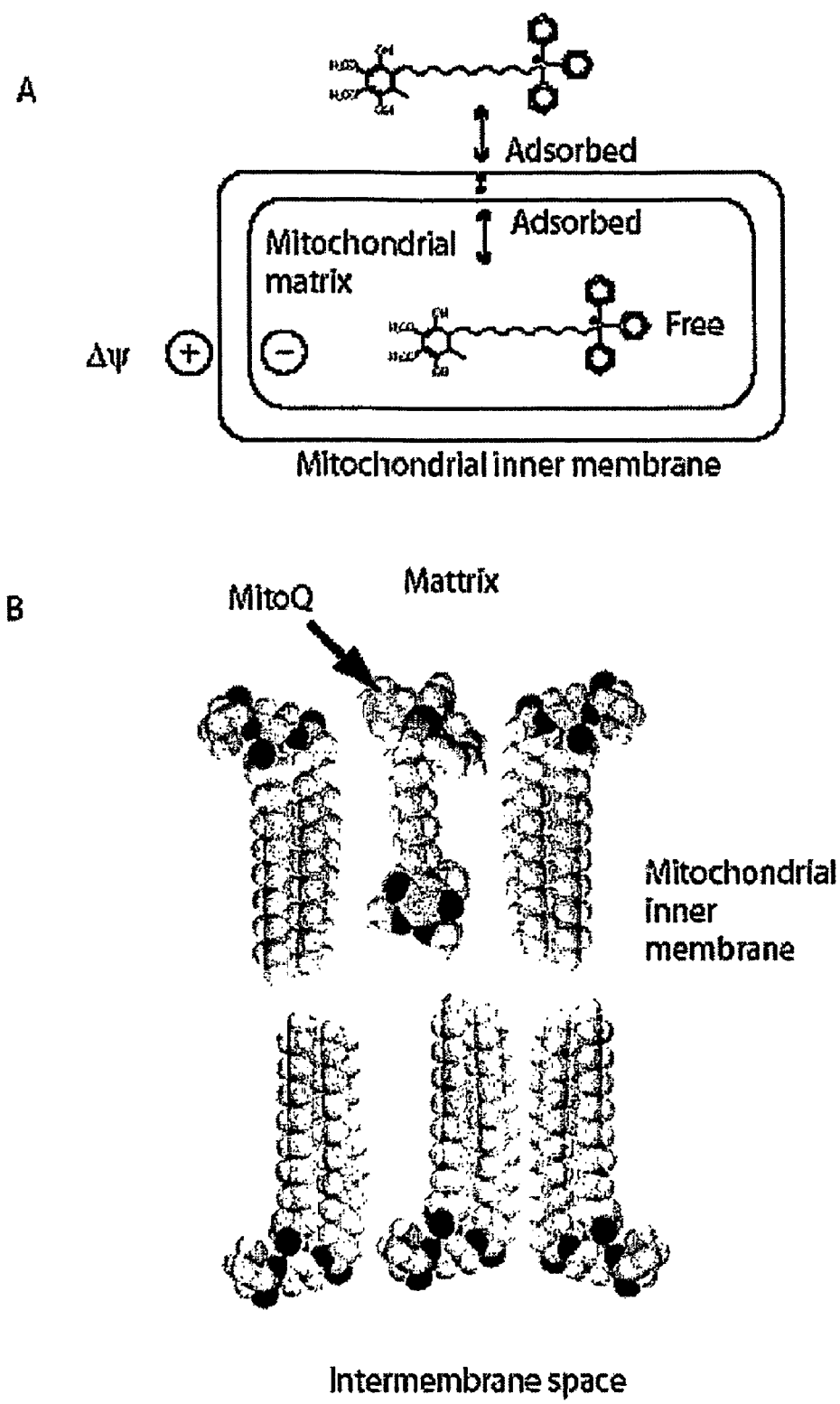
FIG. 1 depicts the uptake of antioxidant compounds by mitochondria. A: The uptake of Mitoquinone-C10 into an energised mitochondrion is shown schematically. B: The position of Mitoquinone-C10 adsorbed to the matrix surface of the inner membrane is shown relative to a simple phospholipid with the triphenylphosphonium moiety adsorbed to the membrane surface at the level of the fatty acid carbonyls, with the methylene bridge and ubiquinol moiety inserted into the hydrophobic core of the phospholipid bilayer.

As stated above, the focus of this invention is on the mitochondrial targeting of compounds, primarily for the purpose of therapy and/or prophylaxis to reduce oxidative stress.

Mitochondria have a substantial membrane potential of up to 180 mV across their inner membrane (negative inside). Because of this potential, membrane permeant, lipophilic cations accumulate several-hundred fold within the mitochondrial matrix.

The applicants have found that by coupling lipophilic cations (for example the lipophilic triphenylphosphonium cation) to an antioxidant moiety the resulting amphiphilic compound can be delivered to the mitochondrial matrix within intact cells. The antioxidant is then targeted to a primary production site of free radicals and reactive oxygen species within the cell, rather than being randomly dispersed.

The applicant have now further determined that the properties of the antioxidant compound, such as for example the nature of the antioxidant moiety, the physical and chemical characteristics of the linking moiety, such as, for example, the length or lipophilicity of the linking moiety, and/or the nature of the lipophilic cation contribute to the efficacy of the antioxidant compound in vivo and contribute to the antioxidant functionality of the compound. For antioxidant compounds of the present invention, efficacy in vivo may in part comprise suitable bioavailability, suitable stability, suitable antioxidant activity, and/or suitable mitochondrial targeting and/or accumulation. For example, antioxidant compounds of the present invention having as a linking moiety a saturated linear carbon chain of less than 6 carbon atoms exhibit good bioavailability at least in part it is believed (without wishing to be bound by any theory) due to a low partition co-efficient.

For antioxidant compounds of the present invention antioxidant functionality includes antioxidant activity, the location and/or distribution of the antioxidant moiety, and the ability of the antioxidant compound to interact with various mitochondrial compounds including for example, components of the respiratory chain.

Indeed the antioxidant functionality of the antioxidant compound can be varied depending upon the physicochemical properties of the component moieties comprising the antioxidant compound.

For instance, examples of antioxidant compounds with the present invention are amphiphilic, having both a hydrophilic and a hydrophobic part. We believe without wishing to be bound by any theory that this amphiphilicity at least in part confers upon the compounds of the present invention the ability to locate to and reside within desired mitochondrial locations.

In principle, any lipophilic cation and any antioxidant capable of being transported to and/or through the mitochondrial membrane and accumulated at or within the mitochondria of intact cells, can be employed in forming the compounds of the invention.

It is however preferred that the lipophilic cation be the triphenylphosphonium cation herein exemplified. Other lipophilic cations which may covalently be coupled to antioxidants in accordance with the present invention include the tribenzyl ammonium and phosphonium cations. In some examples of antioxidant compounds of the present invention, the lipophilic cation is coupled to the antioxidant moiety by a linear carbon chain having from 1 to about 30 carbon atoms, for example from 2 to about 20, from about 2 to about 15, from about 3 to about 10, or from about 3 to about 6 carbon atoms.

Conveniently the carbon chain is an alkylene group (for example, $C_1$-$C_{20}$, or $C_1$-$C_{15}$), yet carbon chains which optionally include one or more double or triple bonds are also within the scope of the invention. Also included are carbon chains which include one or more substituents (such as hydroxyl, carboxylic acid or amide groups), and/or include one or more side chains or branches, such as those selected from unsubstituted or substituted alkyl, alkenyl, or alkynyl groups. Also included are carbon chains which comprise more than about 30 carbon atoms but whose length is equivalent to a linear saturated carbon chain having from 1 to about 30 carbon atoms.

It will be appreciated by those skilled in the art that moieties other than a straight alkylene may be used to covalently couple the antioxidant moiety to the lipophilic cation, for example, substituted or branched alkyl groups, peptide bonds, and the like.

In some embodiments, the lipophilic cation is linked to the antioxidant moiety by a straight chain alkylene group having 1 to 10 carbon atoms; such as, for example an ethylene, propylene, butylene, pentylene or decylene group.

Antioxidant moieties useful in the present invention include those which require interaction with reductants for antioxidant activity whether for initial antioxidant activity or for the recycling of antioxidant activity, or both For example, antioxidant compounds of the present invention which comprise as the active antioxidant moiety a quinol moiety may be administered in the quinone form. To function as an antioxidant, that is to have antioxidant activity, the quinone must be reduced to the quinol form by interaction with a reductant, such as, for example, a mitochondrial reductant such as Complex II, for initial antioxidant activity. Subsequent interaction of the oxidised quinone form with reductants can lead to recycling of antioxidant activity.

Other examples of antioxidant moieties useful in the present invention include those which exist already as the reduced form and do not require interaction with reductants for initial antioxidant activity. Notwithstanding this, subsequent interaction of the oxidised form of such antioxidant moieties with mitochondrial reductants can lead to the recycling of antioxidant activity. For example, the antioxidant moiety Vitamin E can be administered in the reduced form and so does not require interaction with reductants for initial antioxidant activity, but may subsequently interact with reductants, such as, for example, the endogenous quinone pool, thereby to recycle antioxidant activity.

Further examples of antioxidant moieties useful in the present invention include those that are not recycled by interaction with mitochondrial reductants.

Examples of antioxidant moieties useful in the present invention include vitamin E and vitamin E derivatives, chain breaking antioxidants, such as butylated hydroxyanisole, butylated hydroxytoluene, quinols and general radical scavengers such as derivatised fullerenes. In addition, spin traps, which react with free radicals to generate stable free radicals can also be used. These will include derivatives of 5,5-dimethylpyrroline-N-oxide, tert-butylnitrosobenzene, tert-nitrosobenzene, α-phenyl-tert-butylnitrone and related compounds.

Preferred antioxidant compounds, including those of general formulae I and II herein, can be readily prepared, for example, by the following reaction:

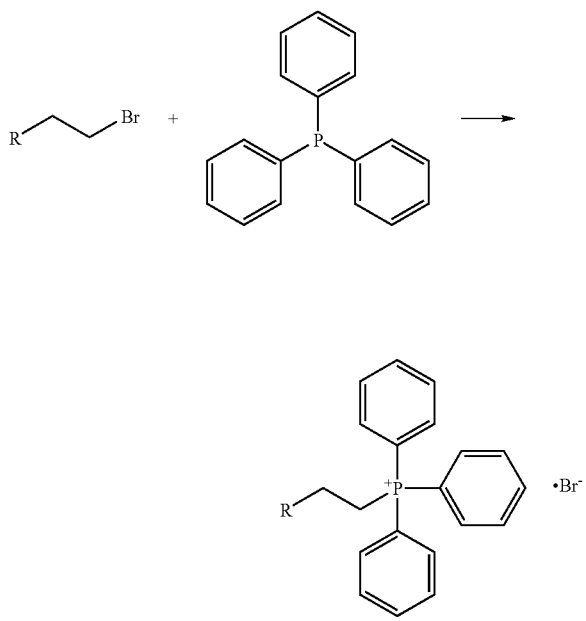

The general synthesis strategy is to heat a precursor containing a suitable leaving group, preferably a alkyl sulfonyl, bromo or iodo precursor with greater than 1 equivalents of triphenylphosphine under argon for several days. The phosphonium compound is then isolated as its salt. To do this the product is triturated repeatedly with diethyl ether until an off-white solid remains. This is then dissolved in chloroform or dichloromethane and precipitated with diethyl ether to remove the excess triphenylphosphine. This is repeated until the solid no longer dissolves in chloroform. At this point the product is recrystallised several times from a suitable solvent such as chloroform, acetone, ethyl acetate or higher alcohols.

Set out below is the synthetic scheme which may be used to prepare a preferred mitochondrially targeted antioxidant compound of the present invention, namely compound (2) (also referred to herein as Mitoquinone-C3).

An overall synthetic route to compound (2) is shown in Schemes 1 and 3 and is based on converting 4,5-dimethoxy-5-methylbenzoquinone ($CoQ_0$) (5) to 2,3,4,5-tetramethoxytoluene (7) then adding a three carbon side chain by metallation and reaction with allyl bromide.

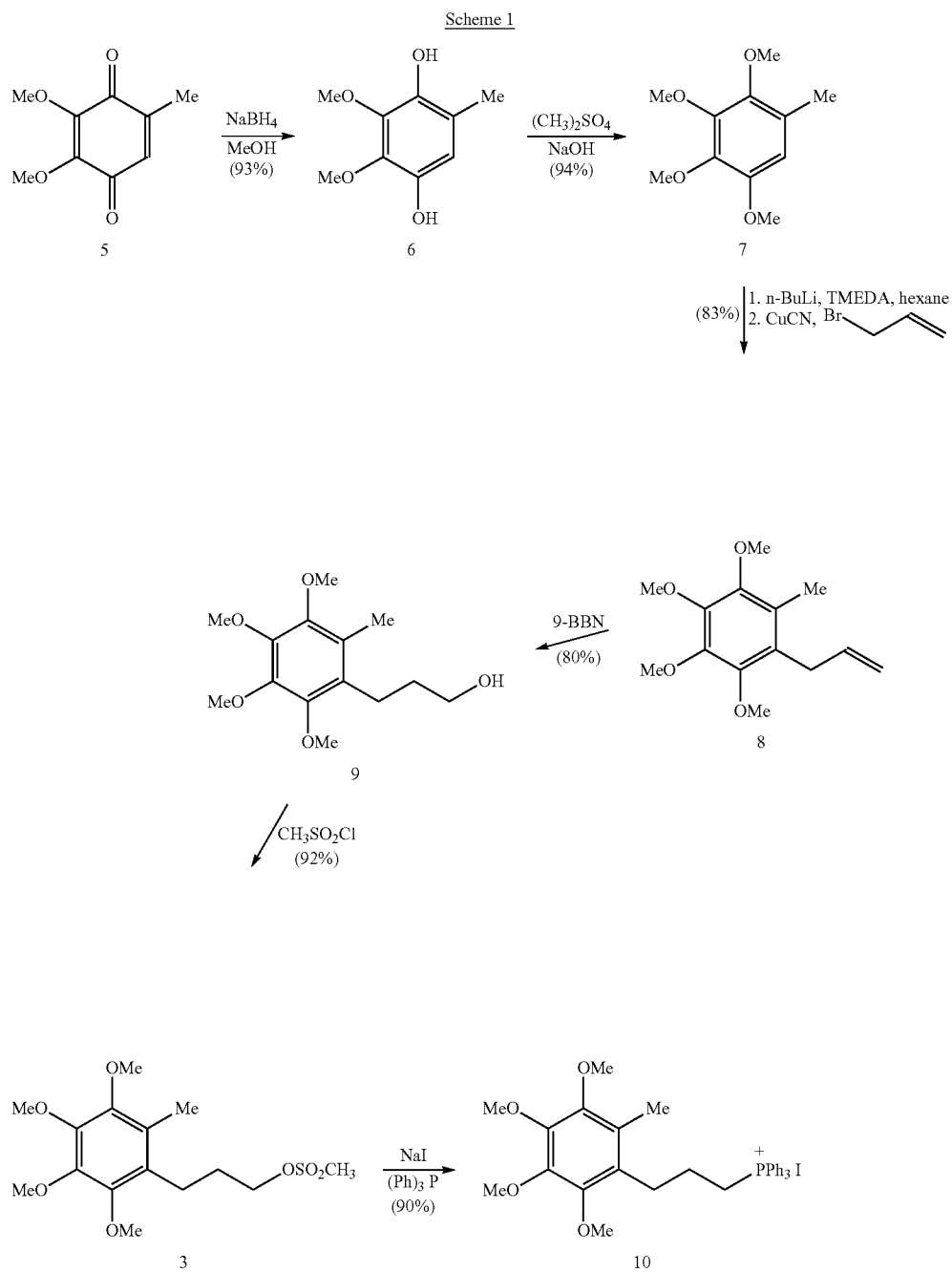

Compound (7) has been prepared by alternative routes based on p-cresol (Keinan, E.; Eren, D., 1987 *J Org Chem*, 52, 3872). There are two possible metallation routes: lithiation of 7 followed by copper-catalysed allylation as shown in Scheme 1 or via the bromo derivative (11) followed by Grignard formation and allylation (Yoshioka, T., Nishi, T., Kanai, T., Aizawa, Y., Wada, K., Fujita, T., and Horikoshi, H. 1993 EP 549366 A1 19930630 CAN 119: 225944) (Scheme 2). Hydroboration of 8 gives the alcohol 9 which is activated as a mesylate (3) and displaced with triphenylphosphine to give the aromatic phosphonium salt 10 iodide. The phosphonium salt formation is best carried out in the absence of solvent using sodium iodide to enhance the reaction.

Scheme 2

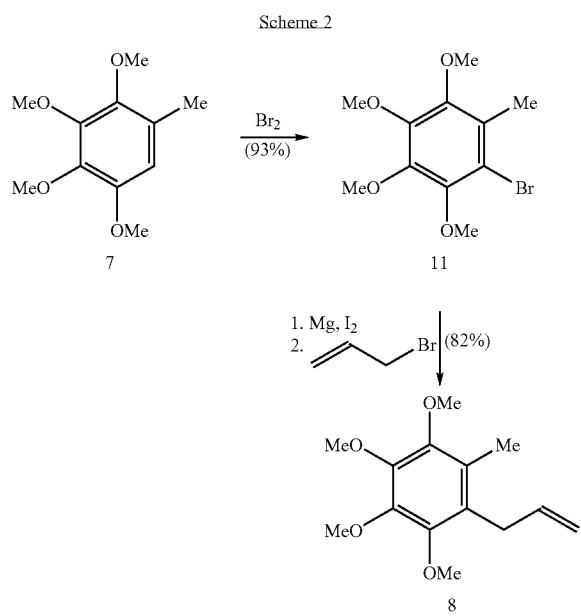

Conversion of the tetramethoxyaromatic ring in 10 into the required dimethoxyquinone (2) is achieved by using ceric ammonium nitrate (CAN) on the nitrate salt of 10 (Scheme 3). The product is obtained as a nitrate salt and anion exchange gives the target molecule $mQ_3$ OMs.

Scheme 3

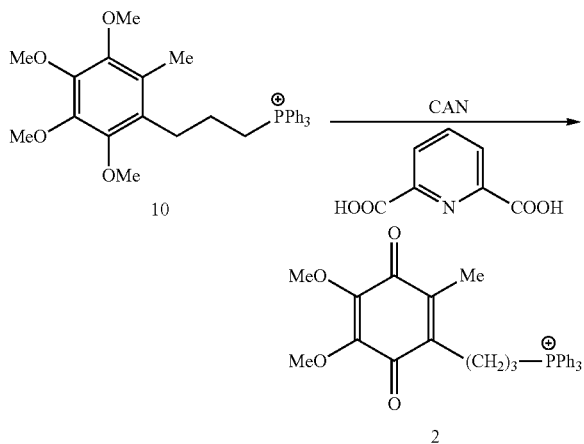

Figure 2A:
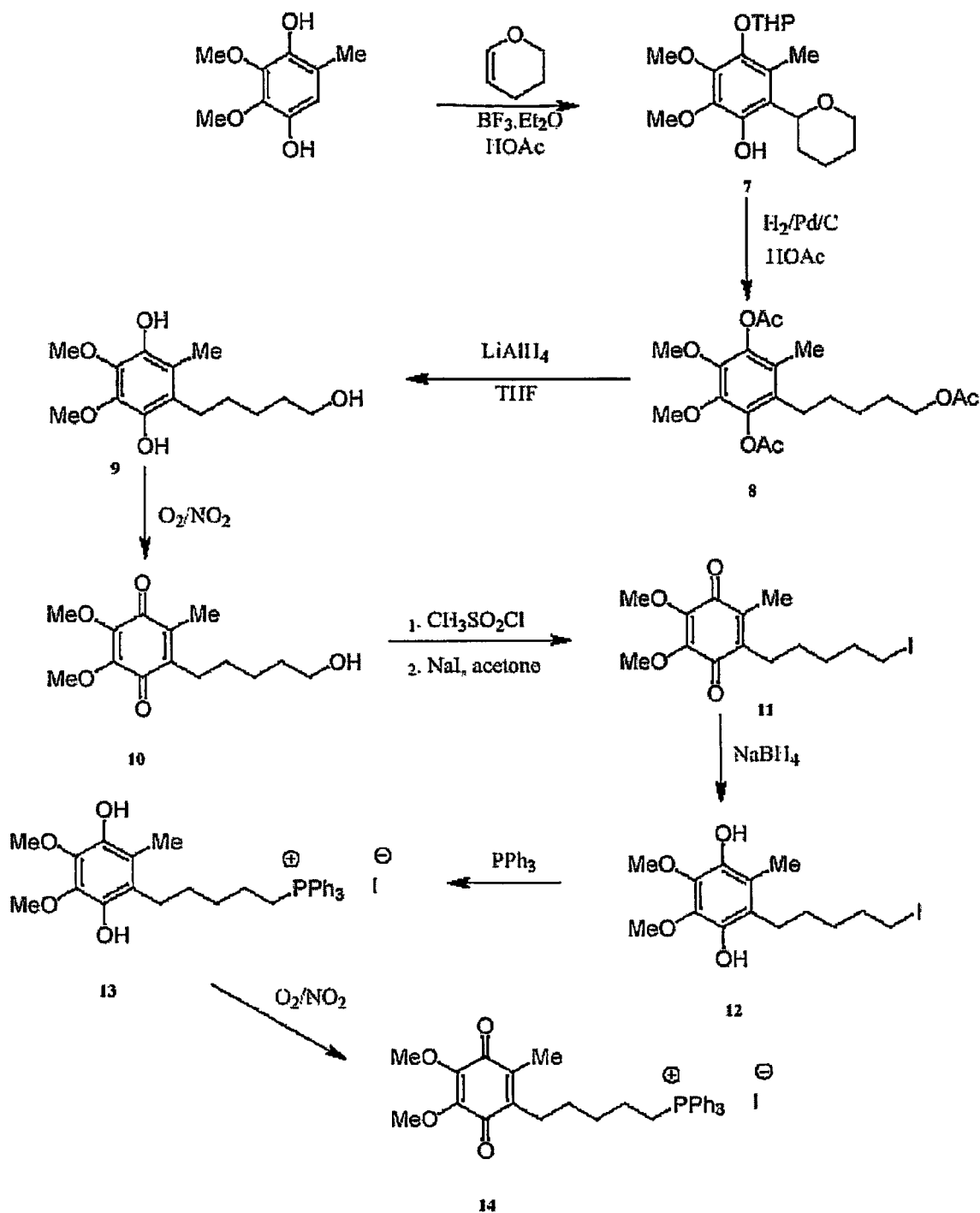
FIG. 2 depicts the synthetic pathways for A: Mitoquinone-C5; B: Mitoquinone-C15.
Figure 2B:
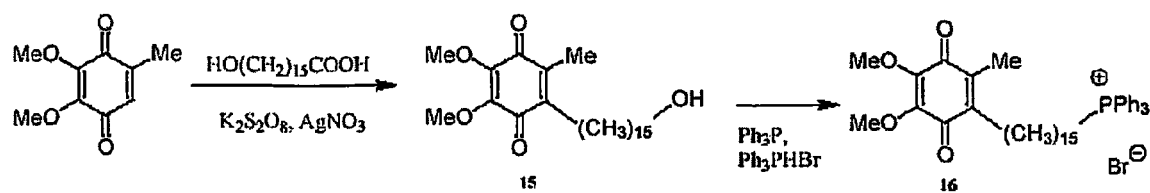

The above synthetic method is described in further detail herein in Example 1. Synthetic methods which may be used to prepare exemplary mitochondrially targeted antioxidant compounds Mitoquinone-C5 and Mitoquinone-C15 are depicted in FIGS. 2A and 2B, respectively, and presented in Example 2 herein.

It will also be appreciated that the anion of the antioxidant compound thus prepared can readily be exchanged with another pharmaceutically or pharmacologically acceptable anion, if this is desirable or necessary, using ion exchange or other techniques known in the art.

The applicants have determined that the stability of the salt form of the antioxidant compound is enhanced when the anion does not exhibit reactivity towards the antioxidant moiety, the linking moiety, or the lipophilic cationic moiety. For example, in the case of preferred examples of antioxidant compounds of the invention, the anion is not nucleophilic. It is also desirable that the anion is a pharmaceutically acceptable anion. It is also preferred that for pharmaceutical formulation the anion does not exhibit reactivity towards any other agents comprising the formulation.

Examples of non-nucleophilic anions include hexafluoroantimonate, -arsenate or -phosphate, or tetraphenylborate, tetra(perfluorophenyl)borate or other tetrafluoroborates, trifluoromethane sulfonate, aryl and alkyl sulfonates such as methanesulfonate and p-toluenesulfonate, and phosphates.

Examples of pharmaceutically acceptable anions include halogen ions such as a fluoride ion, chloride ion, bromide ion and iodide ion; anions of inorganic acid salts such as nitrate, perchlorate, sulfate, phosphate, and carbonate; pharmaceutically acceptable anions of lower alkylsulfonic acid salts such as methanesulfonic acid, and ethanesulfonic acid salts; pharmaceutically acceptable anions of arylsulfonic acid salts such as benzenesulfonic acid, 2-naphthalenesulfonic acid and p-toluenesulfonic acid salts; pharmaceutically acceptable anions of organic acid salts such as trichloroacetic acid, trifluoroacetic acid, hydroxyacetic acid, benzoic acid, mandelic acid, butyric acid, propionic acid, formic acid, fumaric acid, succinic acid, citric acid, tartaric acid, oxalic acid, maleic acid, acetic acid, malic acid, lactic acid, and ascorbic acid salts; and pharmaceutically acceptable anions of acidic amino acid salts such as glutamic acid and asparatic acid salts.

In the case of preferred examples antioxidant compounds of the invention, the halogen anion precursor is exchanged for aryl or alkyl sulphonate anions. Examples include, but are not limited to, benzene sulfonate, p-toluene sulfonate, 2-napthylene sulphonate, methanesulfonate, ethanesulfonate, propanesulfonate. A particularly preferred anion is the methanesulfonate anion.

The same general procedure can be used to make a wide range of mitochondrially targeted compounds with different antioxidant moieties R attached to the triphenylphosphonium (or other lipophilic cationic) moiety or moieties. These will include a series of vitamin E derivatives, in which the length of the bridge coupling the Vitamin-E function with the triphenylphosphonium (or other lipohilic cationic) moiety is varied. Other antioxidants which can be used as R include chain breaking antioxidants, such as butylated hydroxyanisole, butylated hydroxytoluene, quinols and general radical scavengers such as derivatised fullerenes. In addition, spin traps, which react with free radicals to generate stable free radicals can also be synthesized. These will include derivatives of 5,5-dimethylpyrroline-N-oxide, tert-butylnitrosobenzene, tert-nitrosobenzene, α-phenyl-tert-butylnitrone and related compounds.

It will be appreciated that for an antioxidant compound of the present invention, as for any drug, activity in vitro is by no means the sole determinant of efficacy in vivo. The antioxidant activity of the antioxidant compounds of the present invention can be determined by methods such as those described herein using, for example, isolated mitochondria and/or isolated cells. Whilst it is true that, to be useful as a mitochondrially targeted antioxidant compound of the present invention, an antioxidant compound must exhibit a suitably high antioxidant activity in such assays, to be efficacious in vivo the mitochondrially targeted antioxidant compound must exhibit other desirable physicochemical properties, for example, suitable bioavailability, stability, or antioxidant functionality.

Examples of antioxidant compounds that show good antioxidant activity yet exhibit poor bioavailability with respect to the target compartment in vivo include Coenzyme Q (CoQ) and Idebenone. Both of these compounds must be administered at very high dose rates (for example, 0.5-1.2 g) to obtain minimal clinical effects in human patients.

Examples of the mitochondrially targeted antioxidant compounds of the present invention exhibit good antioxidant activity and bioavailability and thereby are efficacious in vivo at low dose rates. We believe the antioxidant compounds of the present invention to be effective at mitochondrial targeting, whilst exhibiting one or more of the additional benefits of being available as a crystalline or solid form or being able to be formulated as a solid form stability, enhanced bioavailability, and/or modifiable antioxidant functionality. The physical and chemical characteristics, of the antioxidant compounds of the present invention we believe, again without wishing to be bound by any theory, confer upon the antioxidant compounds of the present invention preferred characteristics, thereby enabling their use in compositions, formulations and methods amongst other applications to which the antioxidant compounds of the prior art may be less suitable given their chemical and physical properties.

Examples of antioxidant compounds of the present invention are synthesised such that their physicochemical properties determine their antioxidant functionality, such as their interaction with various mitochondrial components. For example, the Applicants believe (without wishing to be bound by any theory) that the amphiphilicity of, for example, Mitoquinone-C10 at least in part prevents its interaction with and oxidation by complex I of the respiratory chain, rendering this molecule a poor substrate for oxidation. The relative rate of reduction by the respiratory chain of the exemplary compound Mitoquinone-C10 is greater than the rate of oxidation, such that the pool of reduced Mitoquinone-C10 having antioxidant activity is greater than the pool of oxidised Mitoquinone-C10. In contrast, the antioxidant molecule idebenone is a competent substrate of complex I, such that the pool of reduced idebenone, having antioxidant activity is roughly equivalent to the pool of oxidised idebenone which does not have antioxidant activity. It is to antioxidants of improved antioxidant functionality that the present invention is in part directed.

Figure 3:
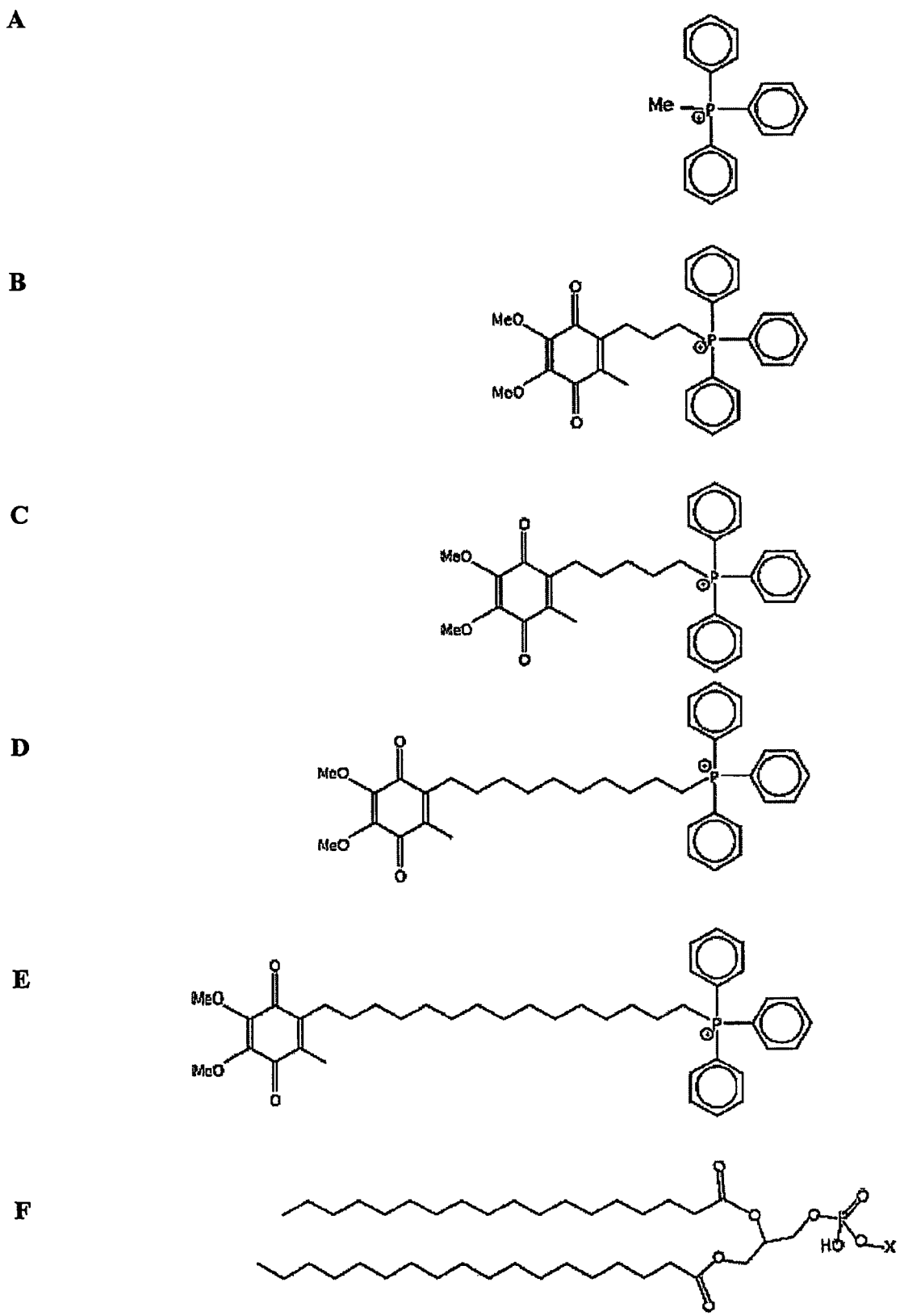
FIG. 3 depicts the structure of Mitoquinone antioxidant compounds and the related compound TPMP. A phospholipid drawn to the same scale is aligned with the Mitoquinone antioxidant compounds to indicate potential maximum depths of penetration of the ubiquinol side chain into one leaflet of a phospholipid bilayer. A: TPMP. B: Mitoquinone-C3. C: Mitoquinone-C5. D: Mitoquininone-C10. E: Mitoquinone-C15. F: phospholipid.

In some embodiments of the invention, the antioxidant compound is a quinol derivative of the formula I defined above. For example, a quinol derivative of the invention is the compound Mitoquinone-C10 as defined above. A further example of a compound of the invention is a compound of formula I in which $(C)_n$ is $(CH_2)_5$, and the quinol moiety is the same as that of Mitoquinone-C10, herein referred to as Mitoquinone-C5 (see FIG. 3C). Yet a further example of a compound of the invention is a compound of formula I in which $(C)_n$ is $(CH_2)_3$, and the quinol moiety is the same as that of Mitoquinone-C10, which is referred to herein as Mitoquinone-C3 or compound 2 (see FIG. 3B). Still a further example of a compound of the invention is a compound of formula I in which $(C)_n$ is $(CH_2)_{15}$, and the quinol moiety is the same as that of Mitoquinone-C10, herein referred to as Mitoquinone-C15 (see FIG. 3E).

Once prepared, the antioxidant compound of the invention, in any pharmaceutically appropriate form and optionally including pharmaceutically-acceptable carriers, excipients, diluents, complexation agents, or additives, will be administered to the patient requiring therapy and/or prophylaxis. Once administered, the compound will target the mitochondria within the cell.

Pharmaceutically acceptable carriers, excipients, diluents, complexation agents, or additives may be chosen so as to enhance the stability of the antioxidant compound, or to enhance its bioavailability. Preferably the antioxidant compound of the invention or the formulation or complex thereof will exhibit good bioavailability.

For example, carrier molecules such as cyclodextrin and derivatives thereof are well known in the art for their potential as complexation agents capable of altering the physicochemical attributes of drug molecules. For example, cyclodextrins may stabilize (both thermally and oxidatively), reduce the volatility of, and alter the solubility of, active agents with which they are complexed. Cyclodextrins are cyclic molecules composed of glucopyranose ring units which form toroidal structures. The interior of the cyclodextrin molecule is hydrophobic and the exterior is hydrophilic, making the cyclodextrin molecule water soluble. The degree of solubility can be altered through substitution of the hydroxyl groups on the exterior of the cyclodextrin. Similarly, the hydrophobicity of the interior can be altered through substitution, though generally the hydrophobic nature of the interior allows accommodation of relatively hydrophobic guests within the cavity. Accommodation of one molecule within another is known as complexation and the resulting product is referred to as an inclusion complex. Examples of cyclodextrin derivatives include sulfobutylcyclodextrin, maltosylcyclodextrin, hydroxypropylcyclodextrin, and salts thereof.

The physicochemical properties, including for example the pharmaceutical properties, or the antioxidant compound-cyclodextrin complex then be varied by, for example, variation of the molar ratio of antioxidant compound to cyclodextrin. For example, for the preferred antioxidant compounds of general formula I, the molar ratio of antioxidant compound to cyclodextrin (antioxidant compound: cyclodextrin) may be from about 10:1 to about 1:10, from about 5:1 to about 1:5, from about 4:1 to about 1:4, from about 2:1 to about 1:2, or about 1:1.

Alternatively, the pharmaceutically appropriate form of antioxidant compound may be formulated so as to enhance the stability and bioavailability of the antioxidant compound. For example, enteric coatings may be applied to tablets to prevent the release of the antioxidant compound in the stomach either to reduce the risk of unpleasant side effects or to maintain the stability of the antioxidant compound which might otherwise be subject to degradation of expose to the gastric environment. Most polymers that are used for this purpose are polyacids that function by virtue or the fact that their solubility in aqueous medium is pH-dependent, and they require conditions with a pH higher then normally encountered in the stomach.

One preferable type of oral controlled release structure is enteric coating of a solid dosage form. Enteric coatings promote the compounds remaining physically incorporated in the dosage form for a specified period when exposed to gastric juice. Yet the enteric coatings are designed to disintegrate in intestinal fluid for ready absorption. Delay of absorption is dependent on the rate of transfer through the gastrointestinal tract, and so the rate of gastric emptying is an important factor. For some administrations, a multiple-unit type dosage form, such as granules, may be superior to a single-unit type. Therefore, in one embodiment, antioxidant compounds of the invention may be contained in an enterically coated multiple-unit dosage form. In a more preferable embodiment, the antioxidant compound dosage form is prepared by producing particles having an antioxidant compound-enteric coating agent solid on an inert core material. These granules can result in prolonged absorption of the antioxidant compound with good bioavailability.

Typical enteric coating agents include, but are not limited to, hydroxypropylmethylcellulose phthalate, methacryclic acid-methacrylic acid ester copolymer, polyvinyl acetate-phthalate and cellulose acetate phthalate. Examples of preferred antioxidant compounds of the present invention and/or formulations and/or complexes thereof exhibit advantageous pharmaceutical properties. For example, they are readily formulatable, are chemically and physically stable, or readily water soluble, have low hygroscopicity and exhibit good shelf life.

The invention will now be described in more detail with reference to the following non-limiting experimental section.

Example 1

Synthesis of Exemplary Mitochondrially Targeted Antioxidant Compound, Compound 2

3,4-Dimethoxy-5-methyl-1,4-benzenediol (6) (CAS Reg 3066-90-8)

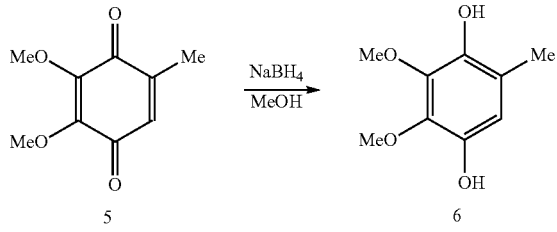

A solution of 2,3-dimethoxy-5-methyl-2,5-cyclohexadiene-1,4-dione (CoQ$_0$) (CAS Reg 605-94-7) (5) (14.62 g, 80.25 mmol) in a mixture of ether (220 mL) and methanol (109 mL) at room temperature was added dropwise to a stirred solution of NaBH$_4$ (15 g, 396 mmol) in H$_2$O (440 mL). The red color of the oxidize (5) was changed to yellow on each addition. After stirring 15 mins at room temperature, the ether phase was separated and the aqueous phase extracted twice with ether (200 mL). The combined ethereal extracts were washed with saturated aqueous NaCl (300 mL), dried (MgSO$_4$), filtered and evaporated in vacuo (20 mm Hg) to give pure 6 as a yellow liquid (13.65 g, 93%).

$^1$H NMR (299.9 MHz) δ 6.48 (1H, s, Ar—H), 3.91, 3.88 (6H, s, Ome), 2.17 (3H, s, Me).

1,2,3,4-Tetramethoxy-5-methyl-benzene (7) (CAS Reg 35896-58-3)

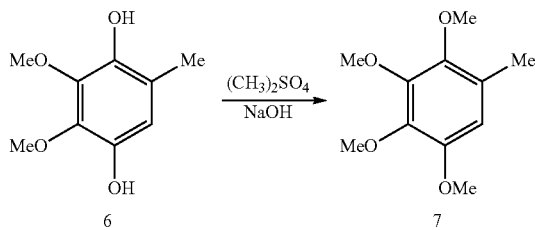

A solution of hydroquinone (6) (5.1 g, 27.7 mmol) in ethanol (40 mL) was prepared at room temperature and an aqueous solution (40 mL) of NaOH (2.6 g) was added in six portions simultaneously with dimethyl sulphate (6 mL) with external room temperature water-cooling. After 45 min, 5% HCl (20 mL) was added and the mixture was extracted with ethyl acetate (3×200 mL). The organic layer washed successively with water and brine, and dried (MgSO$_4$), filtered and then evaporated in vacuo to give a crude product (7) as a red oil (5.5 g). Column chromatography of the crude product on silica gel (100 g, packed in hexane) and elution with 15% ether in hexane afforded pure 7 as a yellow oil (4.95 g, 84%).

$^1$H NMR (299.9 MHz) δ 6.44 (1H, s, Ar—H), 3.93, 3.87, 3.82, 3.79 (12H, s, Ome), 2.23 (3H, s, Me).

1,2,3,4-Tetramethoxy-5-methyl-6-(2-propenyl)benzene (8) (CAS Reg 71573-66-5) via Lithiation (Sakamoto, K., Miyoshi, H., Ohshima, M., Kuwabara, K., Kano, K., Akagi, T., Mogi, T., and Iwamura, H. 1998 *Biochemistry* 37 15106).

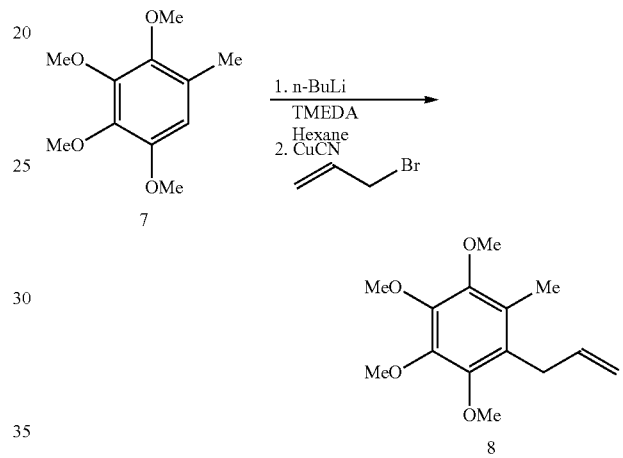

A solution of 7 (6.35 g, 29.9 mmol) in dry hexane (80 mL) and TMEDA (8.6 mL) was placed with a flame-dried stirrer bar in a flame-dried Schlenk tube under nitrogen. A hexanes solution of n-BuLi (1.6M, 26.2 mL) was slowly added at room temperature and the mixture was cooled and stirred at 0° for 1 hr. After being cooled to −78° C., THF (250 mL) was added, and a small aliquot of the reaction mixture was removed, quenched with D$_2$O and examined by $^1$H NMR to assure complete metallation. The yellow suspension was then completely transferred to a second flame-dried Schlenk tube containing CuCN (0.54 g) under nitrogen at −78° C. The mixture was warmed to 0° C. for 10 mins, then cooled to −78° C. and allyl bromide (3.62 mL) was added and the reaction was stirred overnight (19 hrs) and allowed to warm to room temperature. The reaction was quenched with 10% aqueous NH$_4$Cl (75 mL), and extracted with ether (2×200 mL). The combined ethereal extracts were washed with H$_2$O (2×150 mL), 10% aqueous NH$_4$OH (200 mL) and saturated aqueous NaCl (200 mL). The organic solvents were dried over MgSO$_4$, filtered and the solvent removed by rotary evaporation in vacuo to give a crude product (7.25 g). The $^1$H NMR spectrum of this material indicated >93% product formation.

Column chromatography on silica gel and elution with 10:1 hexane:ethyl acetate gave pure 8 (6.05 g, 83.5%).

$^1$H NMR (299.9 MHz) δ 5.84-5.98 (1H, m, —CH=C), 4.88-5.03 (2H, m, =CH$_2$), 3.78, 3.80, 3.90, 3.92 (12H, s, Ome), 3.38 (2H, d, J=Hz, Ar—CH$_2$), 2.14 (3H, s, Me).

1-Bromo-2,3,4,5-tetramethoxy-6-methylbenzene (11) (CAS Reg 73875-27-1)

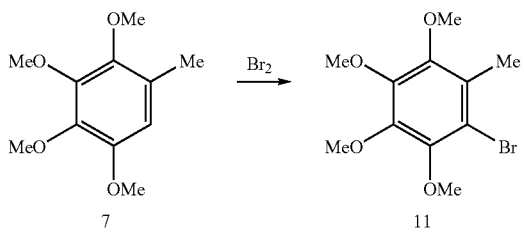

A solution of Br$_2$ (7.92 g, 4.9 mmol) in CH$_2$Cl$_2$ (10 mL) was slowly added to a solution of 7 (10 g, 4.7 mmol) in CH$_2$Cl$_2$ (50 mL) at room temperature over 5 mins. The reaction was stirred for a further 5 mins, by which time t.l.c (20% ether:hexane) showed the reaction to be complete. The reaction was quenched with H$_2$O (50 mL), then washed with 5% aqueous NaOH (50 mL) and saturated NaCl (50 mL). The organic fraction was dried (MgSO$_4$), filtered and the solvent removed in vacuo to give the crude product as an orange oil (13.79 g). Chromatography on silica gel (180 g) and elution with 10% ether:hexane gave pure 11 (12.72 g, 93%) as a pale yellow oil.

$^1$H NMR (299.9 MHz) δ 3.91 (6H, s, Ome), 3.85 (3H, s, Ome), 3.79 (3H, s, Ome), 2.30 (3H, s, Ar-Me).

1,2,3,4-Tetramethoxy-5-methyl-6-(2-propenyl)benzene (8) (CAS Reg 71573-66-5) via Grignard (Yoshioka, T., Nishi, T., Kanai, T., Aizawa, Y., Wada, K., Fujita, T., and Horikoshi, H. 1993 EP 549366 A1 19930630 CAN 119:225944)

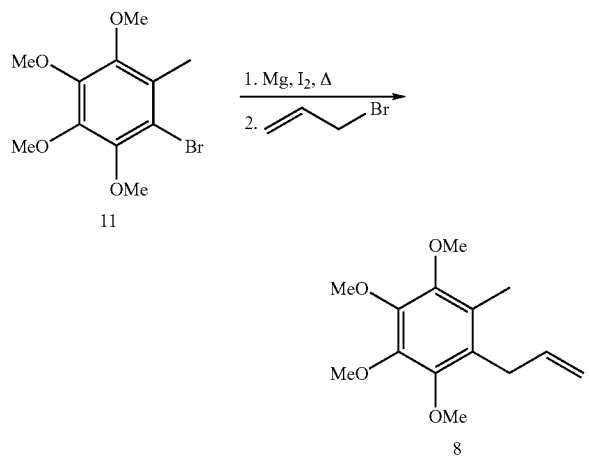

Compound 11 (15.26 g, 5.2 mmol) was dissolved in freshly distilled (Na,K) THF (70 mL) in a flame-dried Schlenk tube under argon. Magnesium (1.91 g, 7.8 mmol) was ground in a mortar and pestle and added to another flame-dried Schlenk tube under argon. The Mg was flame-dried under vacuum and, after cooling, a small amount (~20 mg) of Iodine and freshly distilled THF (10 mL) was added. The magnesium mixture was stirred for 1 min at 45° C. in which time the solution became turbid and then 10 mL of the THF solution of 11 was added under argon via a cannula. The resultant solution quickly lost its turbidity and became pale yellow. The remaining solution of 11 was added in 10 mL portions over 10 mins at 45° C. and then the solution was stirred for a further 20 mins at room temperature. A small aliquot of the reaction mixture was quenched at this time with D$_2$O and t.l.c (20% ether:hexane) showed all of 11 had been reacted. $^1$H NMR indicated 85% deuterium incorporation in the product 7. Allyl bromide (9 mL, 10.4 mmol) was then added by syringe and the reaction was stirred for 3 hrs at room temperature. The solvent was removed in vacuo and saturated aqueous NH$_4$Cl (100 mL) was added. The mixture was then extracted with ethyl acetate (4×100 mL) and the extract dried (MgSO$_4$) and filtered. The solvent was removed in vacuo to give the crude product as a pale orange oil. Purification by silica gel column chromatography (200 g) eluting with 10:1 hexane:ethyl acetate gave 8 (10.30 g, 82%) as a colourless oil together with a small impure fraction.

$^1$H NMR (299.9 MHz) δ 5.84-5.98 (1H, m, CH═C), 4.88-5.03 (2H, m, CH$_2$═C), 3.78, 3.80, 3.90, 3.92, (12H, s, Ome), 3.38 (2H, d, Ar—CH$_2$—C), 2.14 (3H, s, Ar-Me).

3-(2,3,4,5-Tetramethoxy-6-methyl-phenyl)-propan-1-ol (9)

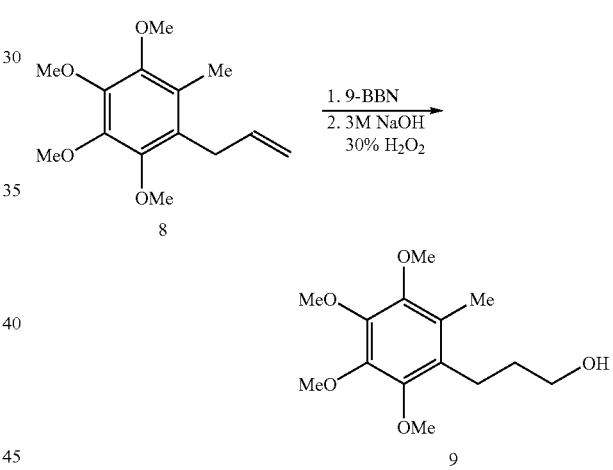

A solution of 8 (8.0 g, 33.05 mmol) in THF (45 mL) was added dropwise over 20 mins under argon to a stirred suspension of 9-borabicyclo[3,3,1]nonane (9-BBN) in THF (79 mL, 39.67 mmol, 0.5M) at 250. The resulting solution was stirred overnight at room temperature and for further 2 hrs at 65° under argon. The mixture was then cooled to 0° and 3M NaOH (53 mL) was then added dropwise followed by 30% aqueous H$_2$O$_2$ (53 mL). After 30 mins stirring at room temperature, the water phase was saturated with NaCl and extracted 3 times with THF. The combined organic fractions were washed with saturated aqueous NaCl, dried (Na$_2$SO$_4$), filtered and evaporated to give an oily residue (11.5 g) which was purified by column chromatography on silica gel (200 g, packed with ether/hexane 1:9). Elution with ether/hexane 1:4 gave pure 9 as viscous, colourless oil (6.85 g, 80%).

$^1$H NMR (299.9 MHz) δ 3.91, 3.90, 3.84, 3.79 (12H, s, Ome), 3.56 (2H, t, J=7.0 Hz, —CH$_2$—OH), 2.72 (2H, t, J=7.0 Hz, Ar—CH$_2$), 2.17 (3H, s, Ar—CH$_3$), 1.74 (2H, quintet, J=7.0 Hz, —CH$_2$—).

1-Methanesulfonyloxy-3-(2,3,4,5-tetramethoxy-6-methyl-phenyl)-propane (3)

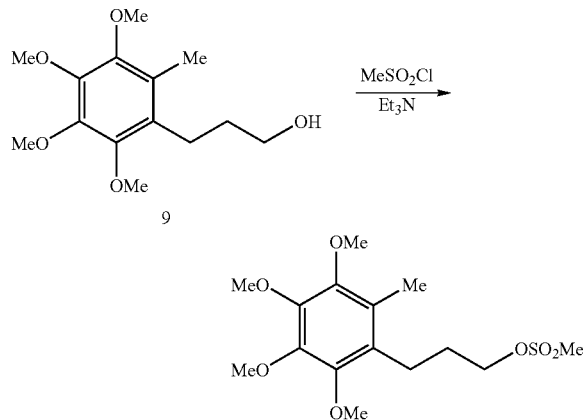

A solution of 9 (3.88 g, 15 mmol) and triethylamine (3.0 g, 30 mmol, 4.2 mL) in CH$_2$Cl$_2$ (50 mL) was stirred at room temperature for 10 mins. Methane sulfonyl chloride (1.8 g, 1.20 mL, 15.75 mmol) in CH$_2$Cl$_2$ (50 mL) was added dropwise over 20 mins and the reaction mixture stirred at room temperature for 1 hr. The mixture was then diluted with CH$_2$Cl$_2$ (50 mL) and the organic layer washed with H$_2$O (5×100 mL), 10% aqueous NaHCO$_3$ (100 mL), dried (MgSO$_4$), filtered and the solvent removed in vacuo by rotary evaporation to afford pure 3 as a liquid (4.8 g, 95%).

$^1$H NMR (299.9 MHz) δ 4.27 (2H, t, J=7.0 Hz, —CH$_2$—O—SO$_2$-Me), 3.91, 3.89, 3.82, 3.78 (12H, s, Ome), 3.03 (3H, s, —O—SO$_2$-Me), 2.70 (2H, t, J=7.0 Hz, Ar—CH$_2$—), 2.17 (3H, s, Me), 1.9 (2H, m, —CH$_2$—).

[3-(2,3,4,5-Tetramethoxy-6-methyl-phenyl)-propyl] triphenylphosphonium iodide (10)

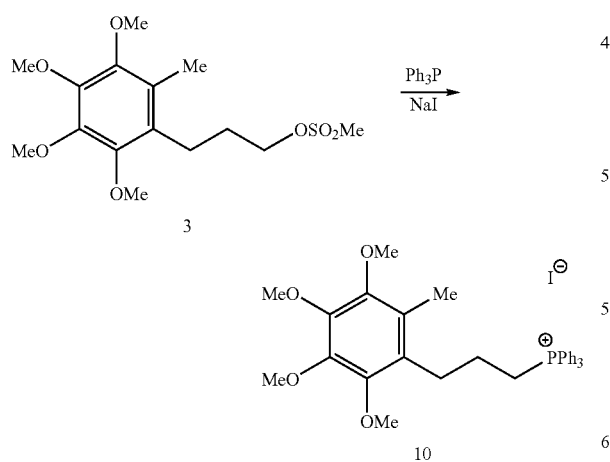

The methanesulfonate 3 (3.30 g, 9.8 mmol) was mixed with a freshly ground mixture of triphenylphosphine (4.08 g, 15.6 mmol) and NaI (7.78 g, 51.9 mmol) in a KIMAX tube and sealed under argon. The mixture was then held at 70-74° C. with magnetic stirring for 3 hrs during which time the mixture changed from a molten thick liquid into a glassy solid. The tube was cooled to room temperature and the residue stirred with CH$_2$Cl$_2$ (30 mL). The suspension was then filtered and the filtrate evaporated in vacuo. The residue was dissolved in a minimum amount of CH$_2$Cl$_2$ and triturated with excess ether (250 mL) to precipitate the white solid. The solid was filtered and washed with ether, dried in vacuo to give pure 10 (5.69 g, 90%).

$^1$H NMR (299.9 MHz) δ 7.82-7.65 (15H, m, Ar—H), 3.88, 3.86, 3.74, 3.73 (12H, s, Ome), 3.76-3.88 (2H, m, CH$_2$—P$^+$), 2.98 (2H, t, J=7.0 Hz, CH$_2$—Ar), 2.13 (3H, s, Ar—CH$_3$), 1.92-1.78 (2H, m, —CH$_2$—). $^{31}$P NMR (121.4 MHz) δ 25.32 (—CH$_2$—P$^+$Ph$_3$).

[3-(2,3,4,5-Tetramethoxy-6-methyl-phenyl)-propyl] triphenylphosphonium nitrate (10)

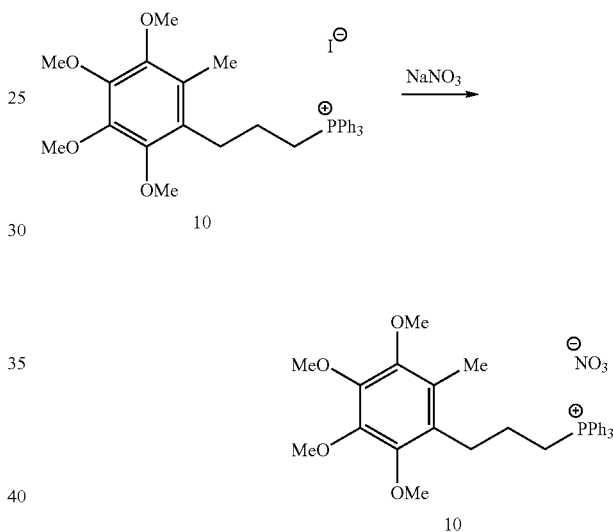

A solution of the iodide form of 10 (4.963 g, 7.8 mmol) in CH$_2$Cl$_2$ (80 mL) was shaken with 10% aqueous NaNO$_3$ (50 mL) in a seporatory funnel for 5 mins. The organic layer was separated, dried (Na$_2$SO$_4$), filtered and evaporated in vacuo to give the crude nitrate form of 10 (4.5 g, 100%).

[3-(4,5-Dimethoxy-2-methyl-3,6-dioxo-1,4-cyclohexadien-1-yl)propyl]triphenylphosphonium bromide (2)

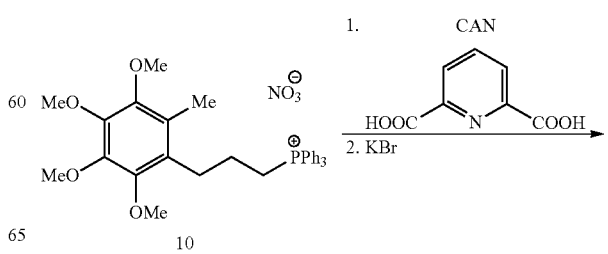

-continued

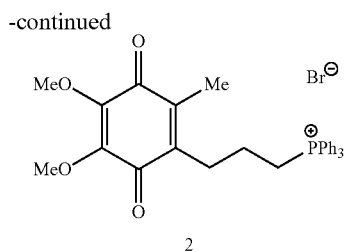

The nitrate form of 10 (4.5 g, 7.8 mmol) was dissolved in a mixture of $CH_3CN$ and $H_2O$ (7:3, 38 mL) and stirred at 0° C. in an ice bath. Pyridine-2,6-dicarboxylic acid (6.4 g, 39 mmol) was then added followed by drop wise addition of a solution of ceric ammonium nitrate (21.0 g, 39 mmol) in $CH_3CN/H_2O$ (1:1, 77 mL) over 5 mins. The reaction mixture was stirred at 0° C. for 20 mins and then at room temperature for a further 10 mins. The reaction mixture was then poured into $H_2O$ (200 mL) and extracted with $CH_2Cl_2$ (200 mL), dried ($Na_2SO_4$), filtered and evaporated in vacuo to give a crude 2 nitrate. The total product was dissolved in $CH_2Cl_2$ (100 mL) and shaken for 10 mins with 20% aqueous KBr (50 mL). The organic layer was separated, dried and evaporated in vacuo to give NMR pure 2 bromide (4.1 g, 93.6%).

$^1$H NMR (299.9 MHz) δ 7.90-7.65 (15H, m, Ar—H), 4.15-4.05 (2H, m, $CH_2$—$P^+$), 3.96, 3.95, (6H, s, Ome), 2.93 (2H, t, J=7.0 Hz, $CH_2$—Ar), 2.15 (3H, s, Ar—$CH_3$), 1.85-1.70 (2H, m, —$CH_2$—). $^{31}$P NMR (121.4 MHz) δ 25.29 (—$CH_2$—$P^+Ph_3$).

[3-(4,5-Dimethoxy-2-methyl-3,6-dioxo-1,4-cyclohexadien-1-yl)propyl]triphenylphosphonium methane sulfonate (2)

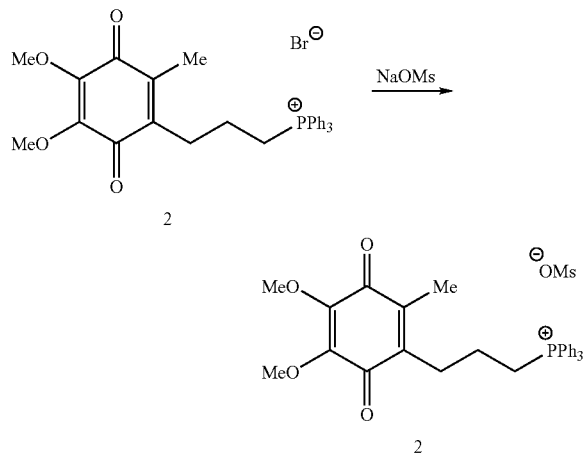

A solution of 2 bromide (3.65 g, 6.5 mmol) in $CH_2Cl_2$ (75 mL) was shaken with an aqueous solution of sodium methane sulphonate (100 mL) in a seporatory funnel for 5 mins. The $CH_2Cl_2$ layer was separated, dried ($Na_2SO_4$), filtered and evaporated in vacuo to give the methane sulfonate salt of 2 (3.7 g, 98%).

$^1$H NMR (299.9 MHz) δ 7.88-7.60 (15H, m, Ar—H), 3.93, 3.92, (6H, s, Ome), 3.90-3.78 (2H, m, $CH_2$—$P^+$), 2.85 (2H, t, J=7.0 Hz, $CH_2$—Ar), 2.70 (3H, s, $OSO_2CH_3$), 2.09 (3H, s, Ar—$CH_3$), 1.82-1.68 (2H, m, —$CH_2$—). $^{31}$P NMR (121.4 MHz) δ 25.26 (—$CH_2$—$P^+Ph_3$).

Example 2

Synthesis of Exemplary Mitochondrially Targeted Antioxidant Compounds, Mitoquinone-C5 and Mitoquinone-C15

The chemical syntheses of Mitoquinone-C5 and Mitoquinone-C15 are outlined in FIG. 2 and are described below. Nuclear magnetic resonance spectra were acquired using a Varian 300 MHz instrument. For $^1$H-NMR tetramethylsilane was the internal standard in $CDCl_3$. For $^{31}$P NMR 85% phosphoric acid was the external standard. Chemical shifts (δ) are in ppm relative to the standard. Elemental analyses were done by the Campbell Microanalytical Laboratory, University of Otago. Electrospray mass spectrometry was done using a Shimadzu LCMS-QP800X liquid chromatography mass spectrometer. Stock solutions were prepared in absolute ethanol and stored at −20° C. in the dark.

Mitoquinone-C5 (14). The synthetic route to Mitoquinone-C5 is shown in FIG. 2A. Dihydropyran (46.83 g, 0.55 mol) was added to 2,3-dimethoxy-5-methyl-1,4-benzohydroquinone ($CoQ_0$) (50 g, 0.275 mol) dissolved in acetic acid (500 mL) and stirred at room temperature for 10 minutes. To this solution was added $BF_3.Et_2O$ (38.57 g, 0.271 mol). The resulting solution was stirred for 18 hours at room temperature. After this time the crude reaction mixture was poured into iced water (500 mL) and extracted with chloroform (1000 mL). The organic extract washed with brine (500 mL) and dried ($MgSO_4$). The solvent was removed in vacuo to give the crude 2,3-dimethoxy-5-methyl-6-(tetrahydro-pyran-2-yl)-4-(tetrahydro-pyran-2-yloxy)-phenol(7) as a red oil (115 g) which was used without further purification. A solution of crude 7 (110 g) in a mixture of acetic acid/perchloric acid (97.5:2.5, 500 mL) was hydrogenated over 5% palladium/charcoal (5.42 g) at atmospheric pressure and room temperature until hydrogen uptake ceased (three days). The reaction mixture was then filtered through a pad of Celite, and the solid residue washed with ethanol (500 mL). The combined filtrate was divided into three equal portions and each portion added to distilled water (1000 mL) and extracted with $CH_2Cl_2$ (2×200 mL). The combined organic extracts were washed with brine (500 ml), saturated sodium bicarbonate (500 mL), brine (300 mL) and then dried ($MgSO_4$). The mixture was then filtered and solvents were removed in vacuo to give crude 4-acetoxy-3-(5-acetoxy-pentyl)-5,6-dimethoxy-2-methyl-phenyl acetate (8) as a red oil (10 g) which was used in the subsequent step without further purification. $^1$H NMR δ 4.0-4.15 (2H, m, —$CH_2$—O), 3.86 (6H, s, 2x OMe), 2.58 (2H, t, J=7.0 Hz, —$CH_2$—Ar), 2.12 (3H, s, Ar-Me), 2.06 (6H, s, 2x $CH_3$—C=O), 2.02 (3H, s, $CH_3$—C=O), 1.35-1.70 (6H, m, —$CH_2CH_2CH_2$—) ppm.

Lithium aluminium hydride (8.0 g, 0.21 mol) was added to dry THF (500 mL) in a 1 L round bottomed flask equipped with a magnetic stirrer, reflux condenser and surrounded by a room temperature water bath. A solution of crude 8 (74 g) in dry freshly distilled THF (100 mL) and was added dropwise to the THF/LiAlH$_4$ mixture over a period of 25-30 minutes. Additional dry THF (200 mL) was added, to facilitate stirring, and the reaction was left stirring for 3 hours at room temperature. The reaction was then quenched by the dropwise addition of 3 M HCl (20 mL) followed by the slow addition of distilled water (70 mL). The reaction mixture was then filtered and the filtrate washed with brine (2×300 mL), dried ($MgSO_4$), filtered and the solvent removed in vacuo. The green residue remaining in the filter funnel was dissolved in 15% HCl (500 mL) and extracted with $CH_2Cl_2$ (1×300 ml, 2×200 ml). The organic fractions were combined and washed with brine (400 ml), dried ($MgSO_4$), filtered and evaporated in vacuo. This extract was combined with the material from the filtrate workup to give crude 2-(5-hydroxypentyl)-5,6-dimethoxy-3-methyl-benzene-1,4-diol (9)(68.3 g) as a red oil. This product 9 was purified using column chromatography on silica gel, (600 g, packed in 10% ether/$CH_2Cl_2$). Elution with 10% ether/$CH_2Cl_2$ gave some unreacted 8 and 2,3-dimethoxy-5-methyl-1,4-benzohydroquinone starting material. Elution with 20% ether/$CH_2Cl_2$, gave a mixture of 9 and the quinone 10 (14.14 g, 19% from 2,3-dimethoxy-5-methyl-1,4-benzoquinol). Compound 9 was slowly converted to the quinone 10 on standing in air and satisfactory elemental analysis could not be obtained. $^1$H NMR δ 5.41 (1H, s, Ar—OH), 5.38 (1H, s, Ar—OH), 4.88 (6H, s, 2x Ar—OMe), 3.65 (2H, t, J=6.3 Hz, $CH_2$—OH), 2.61 (2H, t, J=6.4 Hz, Ar—$CH_2$), 2.14 (3H, s, Ar-Me), 1.42-1.68 (6H, m, 3x-$CH_2$—) ppm.

A solution of the quinol 9 (7.5 g, 27.7 mmol) in $CH_2Cl_2$ (150 mL) was saturated with oxygen gas at atmospheric pressure and a solution of $NO_2$ in $CH_2Cl_2$ (1 ml, 1.32 M) was added. The reaction was stirred at room temperature under an oxygen atmosphere for 18 hours by which time TLC (40% ether/$CH_2Cl_2$) showed the formation of the quinone 2-(5-hydroxypentyl)-5,6-dimethoxy-3-methyl-[1,4]benzoquinone (10) was complete. The solvent was then removed in vacuo to afford the product 10 (Yu, C. A. and Yu, L. (1982) Biochemistry 21, 4096-4101)(7.40 g) as a red oil. $^1$H NMR δ 3.99 (6H, s, 2x Ar—OMe), 3.65 (2H, t, J=6.3 Hz, $CH_2$—OH), 2.47 (2H, t, J=6.3 Hz, Ar—$CH_2$), 2.01 (3H, s, Ar-Me), 1.52-1.60 (2H, m, —$CH_2$—), 1.37-1.43 (4H, m, —$CH_2CH_2$—) ppm.

A solution of 10 (7.40 g, 27.3 mmol) in $CH_2Cl_2$ (150 mL) and triethylamine (5.46 g, 5.46 mmol) was prepared and a solution of methanesulfonyl chloride (2.48 g, 30 mmol) in $CH_2Cl_2$ (50mL) was added over 30 minutes with stirring. After stirring for an additional 1.5 hours at room temperature the reaction mixture washed with distilled water (5×100 mL), saturated sodium bicarbonate (150 mL) and dried ($MgSO_4$). The mixture was filtered and solvent removed in vacuo to give the crude methanesulfonate (9.03 g) as a red oil. $^1$H NMR δ 4.19 (2H, t, J=7.5 Hz, —$CH_2$—OMs), 3.95 (6H, s, 2x Ar—OMe), 2.98 (3H, S, $OSO_2CH_3$), 2.44 (2H, t, J=7.5 Hz, Ar—$CH_2$—), 1.98 (3H, s, Ar-Me), 1.75 (2H, quintet, J=7.5 Hz, —$CH_2$—), 1.38-1.48 (4H, m, —$CH_2$—$CH_2$—) ppm. The methanesulfonate was dissolved in 10% (w/v) NaI in acetone (100 mL) and stirred for 44 hours at room temperature. The mixture was then concentrated in vacuo and $H_2O$ (100 mL) was added to the residue. The mixture was extracted with $CH_2Cl_2$ (3×70 mL) and the combined organic extracts were washed with brine, dried ($MgSO_4$), filtered and the solvent was removed in vacuo to give crude 2-(5-iodopentyl)-5,6-dimethoxy-3-methyl-[1,4]benzoquinone (11). This product was purified by column chromatography on silica gel (150 g). Elution with $CH_2Cl_2$ and 10% ether/$CH_2Cl_2$ gave pure 11 (7.05 g, 69%) as a red oil. $^1$H NMR δ 3.99 (6H, s, 2x Ar—OMe), 3.18 (2H, t, J=6.9 Hz, $CH_2$—I), 2.47 (2H, t, J=7.2 Hz, Ar—$CH_2$), 2.02 (3H, s, Ar-Me), 1.85 (2H, quintet, J=7.5 Hz, —$CH_2$—), 1.38-1.48 (4H, m, —$CH_2$—$CH_2$—) ppm. Anal. calcd. For $C_{14}H_{19}IO_4$: C, 44.5; H, 5.1; I, 33.6. Found: C, 44.6; H, 5.1; I, 33.4%.

A solution of 11 (1.14 g, 2.87 mmol) in methanol (20 ml) was treated with $NaBH_4$ (0.16 g, 4.3 mmol) and the mixture turned colourless within 1 minute. After 5 minutes at room temperature 5% aqueous HCl (100 mL) was added and the solution was extracted with $CH_2Cl_2$ (2×50 mL). The organic fractions were combined, dried ($MgSO_4$), filtered and the solvent removed in vacuo to give 12 (1.15 g, 100%) as an oxygen sensitive yellow oil which was used without delay. $^1$H NMR δ 5.36, 5.31 (2H, s, Ar—OH), 3.89 (6H, s, 2x Ar—OMe), 3.20 (2H, t, J=7.5 Hz, —$CH_2$—I), 2.62 (2H, t, J=7.5 Hz, —$CH_2$—Ar), 2.15 (3H, s, Me), 1.82-1.92 (2H, m, —$CH_2$—), 1.45-1.55 (4H, m, —$CH_2$—$CH_2$—) ppm. A mixture of 12 (1.15 g, 2.87 mmol) and triphenylphosphine (1.2 g, 4.31 mmol) was placed in a Kimax tube with a stirrer bar. The tube was flushed with argon, firmly sealed and heated and stirred for 14 hrs at 70° C. A dark solid was formed which dissolved in $CH_2Cl_2$ (10 mL) and triturated in ether (200 mL) and the white precipitate formed was filtered rapidly. The precipitate, which became sticky on exposure to air, was re-dissolved in $CH_2Cl_2$ and evaporated in vacuo to give the crude product [5-(2,5-dihydroxy-3,4-dimethoxy-6-methyl-phenyl)-pentyl]triphenylphosphonium iodide (13) (2.07 g, 115%) as a brown oil. The material was not stable on storage for extended periods and was used as soon as practicable for subsequent reactions. $^1$H NMR δ 7.84-7.68 (15H, m, Ar—H), 5.45 (1H, s, Ar—OH), 5.35 (1H, s, Ar—OH), 3.89 (3H, s, Ar—OMe), 3.87 (3H, s, Ar—OMe), 3.65 (2H, m, —$CH_2$—$^+PPh_3$), 2.54 (2H, t, J=7.0 Hz, Ar—$CH_2$), 2.08 (3H, s, Ar-Me), 1.65-1.75 (2H, m, —$CH_2$—), 1.45-1.55 (4H, m, —$CH_2CH_2$—) ppm. $^{31}$P NMR δ 25.43 ppm.

A solution of 13 (2.07 g) in $CH_2Cl_2$ (50 mL) was saturated with oxygen gas and a solution of $NO_2$ in $CH_2Cl_2$ (0.5 mL, 1.32 M) was added. The reaction was then stirred at room temperature under an oxygen atmosphere for 18 hrs. The solvent was removed in vacuo to afford the crude product [5-(4,5-dimethoxy-2-methyl-3,6-dioxo-1,4-cyclohexadien-1-yl)pentyl]triphenylphosphonium iodide (14) as a red oil. This residue was re-dissolved in $CH_2Cl_2$ (10 mL) and triturated in ether (200 mL) to give an initial yellow precipitate which congealed into a red oil in a few minutes. The solvents were decanted and the precipitate dissolved in $CH_2Cl_2$ and the solvent removed in vacuo to give the product (14) (1.866 g) as a red oil. An aliquot (0.880 g) of 14 was purified by column chromatography on silica gel (20 g). Elution with $CH_2Cl_2$ gave some unidentified purple coloured material. Elution with 5% ethanol/$CH_2Cl_2$ gave the pure iodide product 14 (0.606 g) as a red oil. $^1$H NMR δ 7.84-7.68 (15H, m, Ar—H) 3.98 (6H, s, 2x Ar—OMe), 3.65 (2H, m, $CH_2$—P$^+$), 2.40 (2H, t, J=7.5 Hz, Ar—$CH_2$), 2.00 (3H, s, Ar-Me), 1.71 (4H, m, —$CH_2$—), 1.43 (2H, m, —$CH_2$—) ppm. $^{31}$P NMR (121.4 MHz) δ 25.47 ppm. Anal. calcd. for $C_{32}H_{36}IO_4P$: C, 59.8; H, 5.7; I, 19.8; P, 4.8. Found: C, 60.0; H, 5.3; I, 19.7; P, 4.7%.

Mitoquinone-C15 (16). The synthetic route to Mitoquinone-C15 is shown in FIG. 2B. A solution of $K_2S_2O_8$ (0.450 g, 1.66 mmol) in $H_2O$ (25 ml) was added dropwise over 2.5 hours to a stirred suspension of $AgNO_3$ (0.262 g, 1.54 mmol), 16-hydroxyhexadecanoic acid (0.408 g, 1.50 mmol), and 2,3-dimethoxy-5-methyl-1,4-benzoquinone (0.271 g, 1.49 mmol) in $H_2O:CH_3CN$ (1:1, 36 mL) held at 75° C. After stirring for 30 minutes the mixture was cooled and extracted with ether (4×30 mL). The combined organic phase washed with $H_2O$ (2×100 mL), $NaHCO_3$ (1 M, 2×50 mL) and saturated NaCl (2×50 mL). The organic phase was dried ($Na_2SO_4$), filtered and concentrated in vacuo to give a red oil (0.444 g). Column chromatography of the crude oil (silica gel, 15 g) and elution with mixtures of $CH_2Cl_2$ and ether (0%, 5% 20%) gave 2-(15-hydroxypentadecyl)-5,6-dimethoxy-3-methyl-[1,4]benzoquinone (15) (0.192 g, 33%) as a red oil. $^1$H NMR δ 3.99, 3.98 (6H, s, OMe), 3.64 (2H, t, J=6.5 Hz, —$CH_2OH$), 2.45 (2H, t, J=7.5 Hz, —$CH_2$-ring), 1.4-1.2

(26H, m, —$(CH_2)_{13}$—). Anal. Calcd. for $C_{24}H_{40}O_5$: C, 70.6; H, 9.9. Found: C, 70.5; H, 9.8%.

A mixture of triphenylphosphine (0.066 g, 0.25 mmol), $Ph_3PHBr$ (0.086 g, 0.25 mmol) and 15 (0.101 g, 0.25 mmol) was stirred under argon in a sealed Kimax tube at 70° C. for 24 hours, by which time it had turned into a viscous red oil. The residue was dissolved in minimum $CH_2Cl_2$ (0.5 mL) and poured into ether (10 mL) to produce a red oily precipitate. The solvents were then decanted the residue was dissolved in $CH_3OH$ (0.5 mL) and diluted with $H_2O$ (10 mL) containing 48% HBr (1 drop). A red precipitate formed and after the precipitate had settled the supernatant was poured off and the residue washed with $H_2O$ (5 mL). The residue was then dissolved in ethanol (5 mL) and the solvent removed in vacuo. The residue was redissolved in $CH_2Cl_2$ (0.5 mL), diluted with ether (5 mL) and the solvent was decanted and the residue placed in a vacuum system (0.1 mbar) for 24 hours to give [15-(4,5-dimethoxy-2-methyl-3,6-dioxo-1,4-cyclohexadien-1-yl)pentadecyl]triphenylphosphonium bromide (16) (0.111 g, 61%) as a yellow foam which turned to a red oil on contact with air. $^1H$ NMR (299 MHz) δ 7.6-8.0 (15H, m, Ar—H), 3.89 (6H, s, OMe), 3.9 (2H, m, —$CH_2$—P), 2.6 (2H, m, —$CH_2$-ring), 1.7-1.1 (26H, m, —$(CH_2)_{13}$—) ppm. $^{31}P$ NMR (121.4 MHz) δ 25.71 ppm. Electrospray mass spectrometry found ($M^+$) 653, calculated for $C_{42}H_{54}O_4P^+$ 653. Combustion analytical results were unsatisfactory due to inconsistent levels of solvent inclusion.

Example 3

Properties of Mitochondrially Targeted Antioxidant Compounds

The present invention recognises that, in order to be suitable in a wide variety of applications, for example the formulation of dosage forms such as tablets, there is advantage in being able to form a crystalline or solid form of the mitochondrially targeted antioxidant compound. Similarly, it is believed, without wishing to be bound by any theory, that mitochondrially targeted antioxidant compounds with low partition coefficients (octanol:water) may exhibit enhanced bioavailability with respect to those compounds having higher partition coefficients, such that a low partition coefficient is desirable for certain applications, and that the antioxidant functionality of the compounds of the present invention are at least in part determined by their physicochemical properties.

The partition coefficients for a variety of antioxidant compounds are shown in Table 1. Octan-1-ol/PBS partition coefficients were determined by adding 400 nmol of the compound to 2 ml PBS-saturated octan-1-ol and mixing for 30 min at 37° C. with 2 ml octan-1-ol saturated PBS. The concentrations of the compound in the two phases were measured by UV absorption at 268 nm and quantitated from standard curves of the compound in octan-1-ol saturated PBS, or PBS-saturated octan-1-ol (Kelso, G. F., Porteous, C. M., Coulter, C. V., Hughes, G., Porteus, W. K., Ledgerwood, E. C., Smith, R. A. J., and Murphy, M. P., 2001, *J Biol Chem* 276, 4588; Smith, R. A. J., Porteous, C. M., Coulter, C. V., and Murphy, M. P. 1999 *Eur J Biochem* 263, 709). Stock solutions of compounds were prepared in absolute ethanol and stored at −20° C. in the dark. [$^3H$]TPMP was from American Radiolabelled Chemicals Inc, (MO, USA).

Of particular note is the low partition coefficient of compounds with small numbers of carbon atoms bridging the antioxidant moiety and the phosphonium. For example, a compound within the present invention, herein referred to as Mitoquinone-C3, which has a 3 carbon bridge has a partition coefficient approximately 50-fold lower than that observed for the related compound, Mitoquinone-C10 (Table 1).

TABLE 1

Partition coefficients of antioxidants and related compounds

| Compound | Partition coefficient |
|---|---|
| Methyltriphenylphosphonium (TPMP) | [a]0.35 ± 0.02 |
| MitoVit E | [b]7.4 ± 1.6 |
| 4-Bromobutyltriphenylphosphonium | [b]3.83 ± 0.22 |
| 4-Iodobutyltriphenylphosphonium | [c]4.0 ± 0.4 |
| Mitoquinone-C15 | |
| Mitoquinone-C10 | [a]160 ± 9 |
| Mitoquinone-C5 | 13.9 ± 1.9 |
| Mitoquinone-C3 | [c]2.8 ± 0.3 |
| α-Tocopherol | [b]27.4 ± 1.9 |
| Bromodecylubiquinone | [d]310 ± 60 |
| Idebenone | [d]3.1 × $10^3$ |
| Decylubiquinone | [d]3.1 × $10^5$ |
| Coenzyme $Q_0$ | [d]1.33 |
| Coenzyme $Q_1$ | [d]409 |
| Coenzyme $Q_2$ | [d]4.44 × $10^4$ |
| Ubiquinone (Coenzyme $Q_{10}$) | [d]1.82 × $10^{20}$ |
| Ubiquinol | [d]4.53 × $10^{20}$ |
| Decylubiquinol | [d]7.91 × $10^5$ |
| Idebenol | [d]7.82 × $10^3$ |

Data[a-c] are octan-1-ol/phosphate buffered saline partition coefficients determined at 25° C. or 37° C. as described above, or octanol/water partition coefficients[d] calculated using Advanced Chemistry Development (ACD) Software Solaris V4.67 as described in Jauslin, M. L., Wirth, T., Meier, T., and Schoumacher, F., 2002, *Hum Mol Genet* 11, 3055.
[a]Kelso, G. F., Porteous, C. M., Coulter, C. V., Hughes, G., Porteus, W. K., Ledgerwood, E. C., Smith, R. A. J., and Murphy, M. P., 2001, *J Biol Chem* 276, 4588.
[b]Smith, R. A. J., Porteous, C. M., Coulter, C. V., and Murphy, M. P. 1999 *Eur J Biochem* 263, 709.
[c]Smith, R. A. J., Porteous, C. M., Gane, A. M., and Murphy, M. P. 2003 *Proc Nat Acad Sci* 100, 9, 5407.

From their octan-1-ol/PBS partition coefficients it is clear that Mitoquinone-C3, Mitoquinone-C5, Mitoquinone-C10 and Mitoquinone-C15 span a wide range of hydrophobicities. That of Mitoquinone-C3 is similar to the simple, relatively water soluble TPMP cation, while that of Mitoquinone-C15 indicates that it has very low water solubility. Alkyltriphenylphosphonium cations such as Mitoquinone are reported to adsorb onto phospholipid bilayers with the cation at the level of the carboxylic acid groups while the hydrophobic alkyl group penetrates into the hydrophobic core of the membrane (FIG. 1). It is believed that the longer the methylene bridge the deeper the antioxidant ubiquinol will penetrate into the hydrophobic core of membrane. The maximum extent to which penetration into one leaflet of the membrane we believe will occur for these compounds is illustrated in FIG. 2, which shows the Mitoquinone variants aligned with a typical phospholipid. This modelling indicates that the ubiquinol moiety of Mitoquinone-C3 only penetrates close to the membrane surface while those of Mitoquinone-C10 and Mitoquinone-C15 penetrate close to the core of the phospholipid bilayer.

We have synthesised a series of antioxidant compounds with a range of hydrophobicities and depths of penetration into the phospholipid bilayer. We believe these antioxidant compounds will target mitochondria so that the antioxidant moiety resides in a predeterminable position within the mitochondria.

Example 4

Mitochondrial Uptake of Mitochondrially Targeted Compounds

To demonstrate that mitochondrial targeting is effective, the uptake by mitochondria in response to the membrane potential of exemplary antioxidant compounds Mitoquinone-C3, Mitoquinone-C5, Mitoquinone-C10, and Mitoquinone-C15 was determined.

To measure the uptake of antioxidant compounds by energised mitochondria, an ion-selective electrode was constructed (Smith, R. A., Kelso, G. F., James, A. M. and Murphy, M. P. (2004) Meth. Enzymol. 382, 45-67; Davey, G. P., Tipton, K. F. and Murphy, M. P. (1992) Biochem. J. 288, 439-443; Kamo, N., Muratsugu, M., Hongoh, R. and Kobatake, Y. (1979) J. Membr. Biol. 49, 105-121). The electrode and a Ag/AgCl reference electrode were inserted through the airtight Perspex lid of a stirred and thermostatted 3 ml incubation chamber at 30° C., provided with an injection port for the addition of substrates. To measure antioxidant compound uptake, rat liver mitochondria (1 mg protein/ml) were incubated at 30° C. in KCl medium (120 mM KCl, 10 mM HEPES, pH 7.2, 1 mM EGTA) and nigericin (1 μg/ml) and rotenone (8 μg/ml). Succinate (10 mM) and FCCP (500 nM) were added where indicated. The output from the ion-selective electrode was passed to a PowerLab Data acquisition system via a front-end pH amplifier and analysed using Chart software, all from ADInstruments.

Rat liver mitochondria were prepared by homogenisation followed by differential centrifugation in ice-cold buffer containing 250 mM sucrose, 5 mM Tris-HCl, 1 mM EGTA, pH 7.4 (Chappell, J. B. and Hansford, R. G. (1972) in: Subcellular components: preparation and fractionation, pp. 77-91 (Birnie, G. D., Ed.) Butterworths, London). The protein concentration was determined by the biuret assay using BSA as a standard (Gornall, A. G., Bardawill, C. J. and David, M. M. (1949) J. Biol. Chem. 177, 751-766). Mitochondrial membrane potential was measured by adding 500 nM TPMP supplemented with 50 nCi [$^3$H]TPMP to mitochondria suspended in KCl medium (120 mM KCl, 10 mM HEPES, pH 7.2, 1 mM EGTA) at 25° C. (Brand, M. D. (1995) in: Bioenergetics—a practical approach, pp. 39-62 (Brown, G. C. and Cooper, C. E., Eds.) IRL, Oxford). After incubation, the mitochondria were pelleted by centrifugation and the amounts of [$^3$H]TPMP in the supernatant and pellets were quantitated by scintillation counting and the membrane potential calculated assuming a mitochondrial volume of 0.5 μl/mg mitochondrial protein and a TPMP binding correction of 0.4 (Brown, G. C. and Brand, M. D. (1985) Biochem. J. 225, 399-405).

We constructed ion-selective electrodes to measure their steady-state concentrations (Smith, R. A., Kelso, G. F., James, A. M. and Murphy, M. P. (2004) Meth. Enzymol. 382, 45-67; Davey, G. P., Tipton, K. F. and Murphy, M. P. (1992) Biochem. J. 288, 439-443; Kamo, N., Muratsugu, M., Hongoh, R. and Kobatake, Y. (1979) J. Membr. Biol. 49, 105-121). The response of these electrodes to simple triphenylphosphonium cations such as TPMP is Nernstian, with a linear response of electrode voltage to $\log_{10}$[cation concentration] and a slope of 60 mV at 30° C. (Davey, G. P., Tipton, K. F. and Murphy, M. P. (1992) Biochem. J. 288, 439-443; Kamo, N., Muratsugu, M., Hongoh, R. and Kobatake, Y. (1979) J. Membr. Biol. 49, 105-121). The most hydrophilic compound, Mitoquinone-C3, also gave a Nernstian electrode response with a slope close to 60 mV at concentrations above 10 μM. This is illustrated in FIG. 4A, right hand side, by the logarithmic electrode response to sequential additions of 1 μM Mitoquinone-C3 in the absence of mitochondria. For Mitoquinone-C5, Mitoquinone-C10 and Mitoquinone-C15 the electrode also responded rapidly and stably to sequential additions in the absence of mitochondria (FIGS. 4B, 4C, and 4D, respectively, right hand side panels). However in these cases the electrode responses were not Nernstian, we believe due to the greater hydrophobicity of these compounds. Even so, for all four antioxidant compounds the ion-selective electrode enabled the measurement of the free concentrations of the compounds and thus their uptake by mitochondria in real time.

Figure 4:
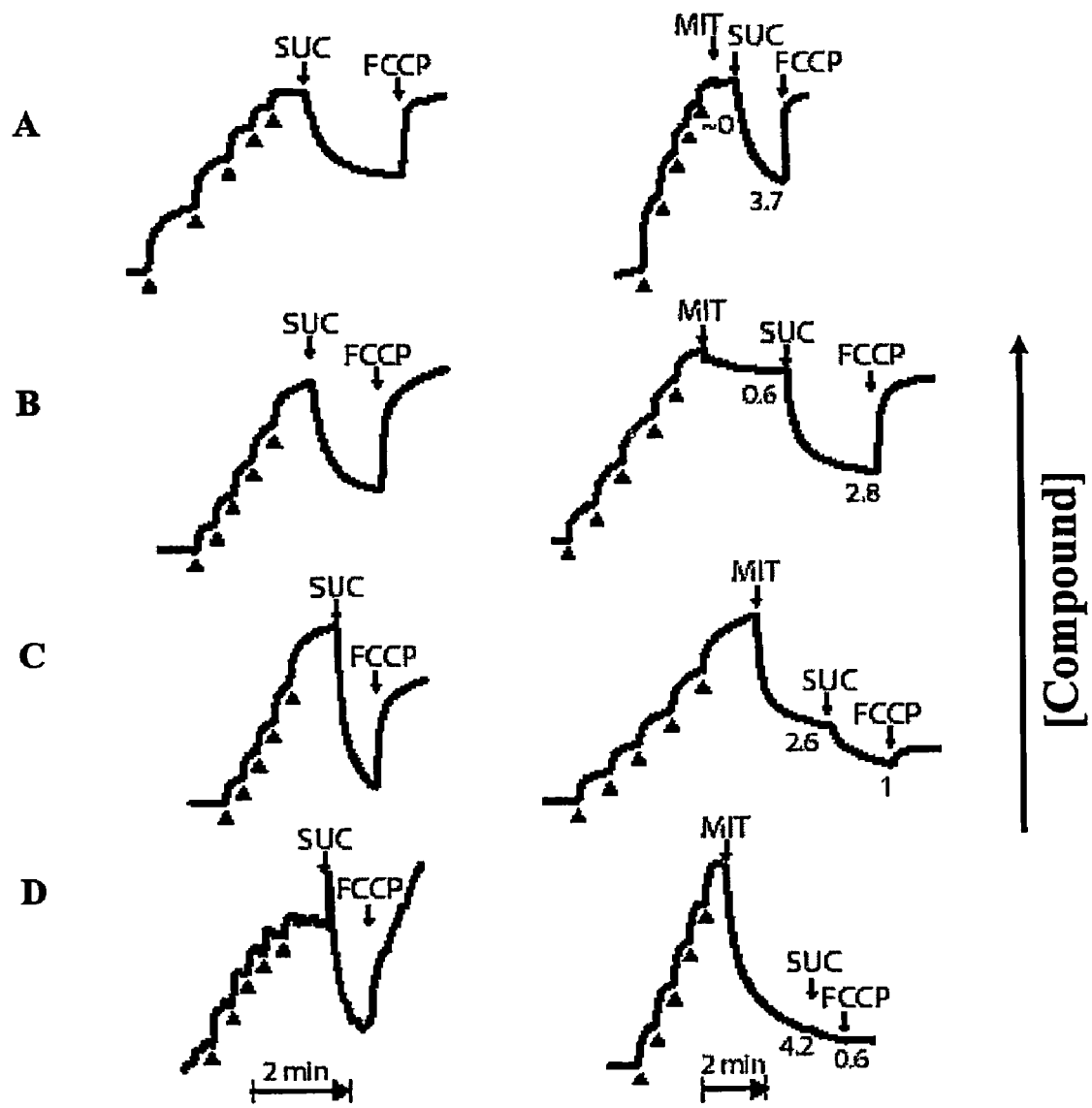
FIG. 4 presents graphs showing the uptake and binding of antioxidant compounds by mitochondria measured using an ion selective electrode. A: Mitoquinone-C3. B: Mitoquinone-C5. C: Mitoquinone-C10. D: Mitoquinone-C15. In the left hand panels mitochondria (1 mg protein/ml) in the presence of rotenone were present and then the antioxidant compounds were added as five sequential 1 µM additions (black arrowheads) to calibrate the electrode response. For the right hand panels the electrodes were first calibrated by five sequential 1 µM additions (black arrowheads) and mitochondria (1 mg protein/ml) were then added. In all cases succinate was added to generate a membrane potential, and FCCP was added to dissipate it. Data are typical traces of experiments repeated at least 2-3 times.

To measure antioxidant compound uptake, mitochondria were added to the electrode chamber in the presence of rotenone to prevent formation of a membrane potential (left side of FIG. 4). We then made five sequential 1 μM additions of antioxidant compound to calibrate the electrode response, followed by the respiratory substrate succinate to generate a membrane potential. Mitochondrial energisation led to the rapid uptake of all the antioxidant compound variants by the mitochondria, and subsequent addition of the uncoupler FCCP abolished the membrane potential and led to their rapid release from the mitochondria (FIG. 4A-D, left side). These experiments clearly show mitochondrial membrane potential-dependent uptake of Mitoquinone-C3, Mitoquinone-C5, and Mitoquinone-C10. While Mitoquinone-C15 was also taken up by mitochondria on induction of a membrane potential, the electrode response to Mitoquinone-C15 in the presence of mitochondria was weaker, noisier and more prone to drift. This contrasts with the electrode response to Mitoquinone-C15 in the absence of mitochondria (cf. right hand panels), and is due to its low free concentrations in the presence of mitochondria.

The extent of antioxidant compound binding to deenergised mitochondria was then determined (FIG. 4, right hand side). For these experiments the antioxidant compound variants were first added to the electrode chamber and then mitochondria were added in the presence of rotenone to prevent formation of a membrane potential. The decrease in antioxidant compound concentration on adding mitochondria is due to binding of antioxidant compound to the deenergised mitochondria. The subsequent addition of succinate to generate a membrane potential indicates the membrane potential dependent uptake of the compounds, which is then reversed by addition of FCCP to abolish the membrane potential.

The free concentration of Mitoquinone-C3 was unaffected by addition of mitochondria, indicating that negligible amounts of Mitoquinone-C3 bound to deenergised mitochondria (FIG. 4A, right hand side). The FCCP-sensitive uptake of mitoquinone-C3 on energisation with succinate was about 3.7 nmol mitoquinone-C3/mg protein, corresponding to an accumulation ratio of ~$2\times10^3$. This is consistent with that expected from the Nernst equation and a mitochondrial membrane potential of about 180 mV, allowing for corrections for intramitochondrial binding.

For Mitoquinone-C5 there was some binding of the compound to the deenergised mitochondria (~0.6 nmol/mg protein), however this was negligible compared to its subsequent uptake on energisation with succinate, of about 2.8 nmol Mitoquinone-C5/mg protein, corresponding to an accumulation ratio of about $1.4\times10^3$ (FIG. 4B, right hand side).

For Mitoquinone-C10 there was significant binding to deenergised mitochondria of about 2.6 mmol Mitoquinone-C10, and this was followed by further uptake of about 1 nmol/mg protein on addition of succinate (FIG. 4C, right hand side).

Nearly all of the free Mitoquinone-C15 was bound to the deenergised mitochondria, but there was some further uptake on energisation with succinate. The membrane potential-dependent uptake of Mitoquinone-C15 was clear on the left hand panel of FIG. 4D, where the electrode response was highly sensitive to enable measurement of the small amount of free Mitoquinone-C15 when the electrode was calibrated in the presence of mitochondria. In contrast, the uptake of Mitoquinone-C15 is difficult to see on the right hand side of FIG. 4D, where the electrode response was far less sensitive to enable measurement of Mitoquinone-C15 in the absence of mitochondria.

These experiments show that the length of the methylene bridges of the antioxidant compounds at least in part determines their extents of adsorption to mitochondrial membranes (right hand side of FIG. 4). The adsorption ranges from negligible for Mitoquinone-C3, to almost complete binding for Mitoquinone-C15. On addition of Mitoquinone-C15 to deenergised mitochondria essentially all the compound binds, distributed across both surfaces of the inner and outer membranes. When a membrane potential is induced we believe there will be significant redistribution of the compound to the matrix-facing surface of the inner membrane from the outer surface of the inner membrane and from the outer membrane. In summary, all the antioxidant compound variants are taken up into mitochondria driven by the membrane potential, and the longer the methylene bridge the greater their adsorption to phospholipid bilayers.

Example 5

Antioxidant Efficacy of Exemplary Mitochondrially Targeted Compounds

Figure 5:
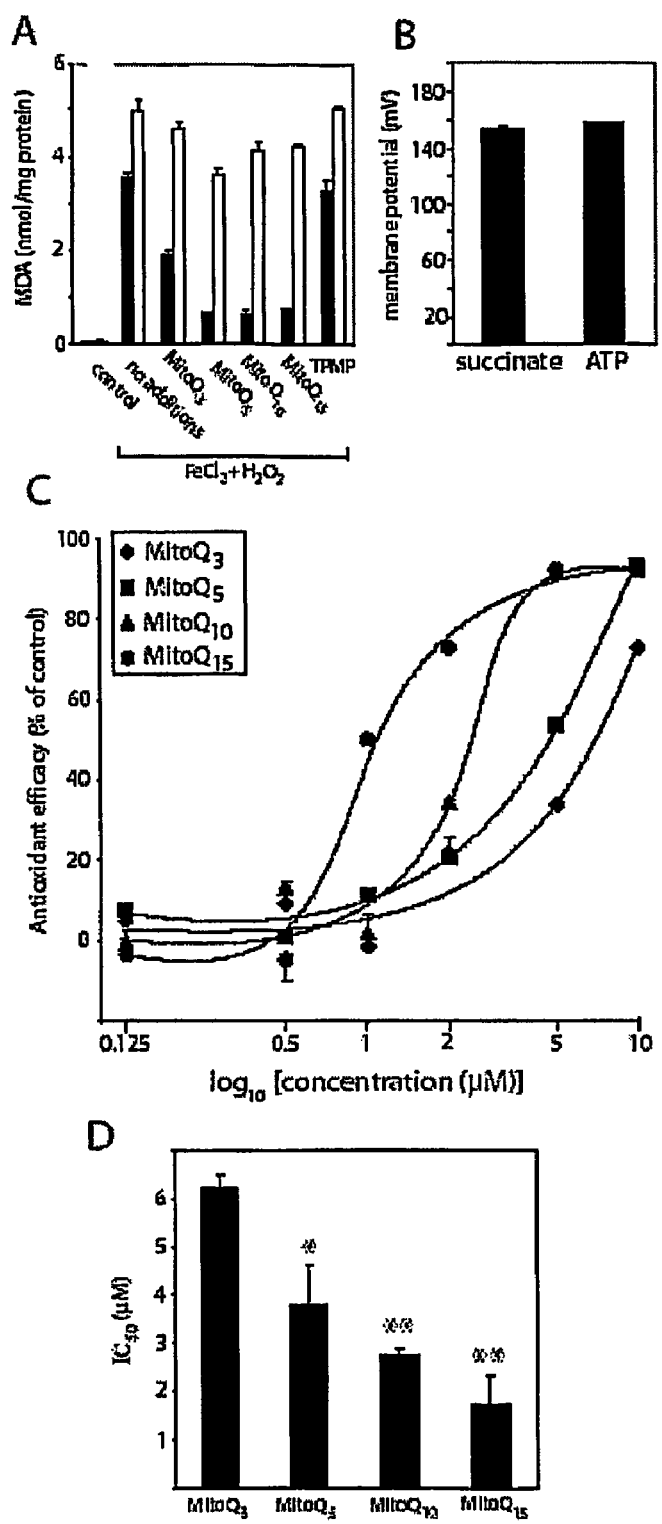
FIG. 5 presents graphs showing the antioxidant efficacy of antioxidant compounds. A: Mitochondria were energised with succinate (black bars) or by incubation with an ATP regenerating system consisting of ATP, phosphoenol pyruvate and pyruvate kinase (white bars). After a 30 sec preincubation with the various Mitoquinone analogues, TPMP or carrier, oxidative stress was induced by addition of 50 µM $FeCl_2$ and 300 µM $H_2O_2$. After 15 min incubation at 37° C., lipid peroxidation was estimated by measuring TBARs. Data are means ±range of two independent experiments. The slight protective effect of Mitoquinone-C5 on lipid peroxidation in the presence of ATP is due to some of the Mitoquinone-C5 added from the stock solution being in the ubiquinol form. B: The mitochondrial membrane potential induced with succinate or with the ATP regenerating system was measured from the accumulation of [$^3$H]TPMP. Data are means±range of duplicate determinations of a 25 minute incubation. The membrane potentials after a 5 minute incubation were the same (data not shown). C: The concentration dependence of the prevention of the accumulation of TBARs by the antioxidant compounds was measured. All incubations were carried out in the presence of succinate as described for A. Results are expressed as % inhibition of TBARS formation, taking the value of a sample exposed to $FeCl_2/H_2O_2$ in the absence of Mitoquinone analogues as 0% inhibition, and a control sample (no $FeCl_2/H_2O_2$ added) as 100%. The data shown are a typical titration with each concentration determined in triplicate ±SD. D: The $IC_{50}$ concentrations for prevention of lipid peroxidation. Data are means ±sem, estimated from three independent titrations as shown in C. The statistical significance relative to the $IC_{50}$ for Mitoquinone-C3 was determined using Student's two tailed t test: *p<0.05; **p<0.005.

The compounds of the invention are also highly effective against oxidative stress. To measure antioxidant efficacy, the ability of the antioxidant compounds to prevent lipid peroxidation in mitochondria, measured from the accumulation of TBARS in mitochondria exposed to ferrous iron and hydrogen peroxide (FIG. 5).

To quantitate lipid peroxidation, the TBARS assay was used. Rat liver mitochondria (2 mg protein/ml) were incubated in 0.8 ml medium containing 100 mM KCl, 10 mM Tris-HCl, pH 7.6 at 37° C., supplemented with either 10 mM succinate and 8 mg/ml rotenone, or an ATP regenerating system of 2.5 mM ATP, 1 mM phosphoenolpyruvate and 4 U/ml pyruvate kinase. The mitochondria were then exposed to oxidative stress by addition of 50 mM $FeCl_2$/300 mM $H_2O_2$ for 15 min at 37° C. After the incubation, 64 ml 2% (w/v) butylated hydroxytoluene in ethanol was added, followed by 200 ml 35% (v/v) $HClO_4$ and 200 ml 1% (w/v) thiobarbituric acid. Samples were then incubated for 15 min at 100° C., centrifuged (5 min at 12,000×g) and the supernatant transferred to a glass tube. After addition of 3 ml water and 3 ml butan-1-ol, samples were vortexed, and the two phases allowed to separate. 200 ml aliquots of the organic layer were then analysed in a fluorometric plate reader ($\lambda_{Ex}$=515 nm; $\lambda_{Em}$=553 nm) for thiobarbituric acid reactive species (TBARS) and compared with a malondialdehyde (MDA) standard curve prepared from 0.01-5 mM 1,1,3,3-tetraethoxypropane (Kelso, G. F., Porteous, C. M., Coulter, C. V., Hughes, G., Porteous, W. K., Ledgerwood, E. C., Smith, R. A. J. and Murphy, M. P. (2001) J. Biol. Chem. 276, 4588-4596).

For mitochondria energised with succinate, the background level of TBARS was negligible, but it increased to about 3.75 nmol MDA/mg protein on exposure to oxidative stress (FIG. 5A; filled bars). High concentrations (5 µM) of any of the antioxidant compounds largely prevented the accumulation of TBARS, while the simple cation TPMP did not. This confirms that it was the ubiquinol side chain of the Mitoquinone antioxidant compounds that was responsible for the antioxidant action, and not any non-specific interactions of the cation with mitochondria.

In these experiments, succinate will both maintain a membrane potential to drive the uptake of the cations into mitochondria, and also recycle the ubiquinone form of the Mitoquinone antioxidant compounds to the active antioxidant ubiquinol form (Kelso, G. F., Porteous, C. M., Coulter, C. V., Hughes, G., Porteous, W. K., Ledgerwood, E. C., Smith, R. A. J. and Murphy, M. P. (2001) J. Biol. Chem. 276, 4588-4596). To see if reduction by the respiratory chain was required for the antioxidant efficacy of the Mitoquinone antioxidant compounds, we incubated mitochondria in the presence of ATP and an ATP regenerating system. ATP hydrolysis and reversal of the mitochondrial ATP synthase led to extensive proton pumping which built up a membrane potential similar to that generated by succinate (FIG. 5B). This will lead to the same Mitoquinone antioxidant compound uptake as for mitochondria energised by succinate, but now the Mitoquinone antioxidant compounds will no longer be recycled to their active ubiquinol forms by the respiratory chain. The Mitoquinone antioxidant compounds were ineffective at preventing lipid peroxidation in mitochondria energised by ATP hydrolysis (FIG. 5a, white bars), compared with the dramatic protection seen in mitochondria energised by succinate (FIG. 5b, black bars). Therefore reduction of Mitoquinone antioxidant compounds by the respiratory chain, as well as accumulation by the mitochondrial membrane potential are required for the antioxidant efficacy of the Mitoquinone antioxidant compounds.

Lower levels of lipid peroxidation were observed in the control samples of mitochondria energised with succinate, compared to those energised with ATP (FIG. 5A). This is due to the protective antioxidant effect of the endogenous mitochondrial Coenzyme Q pool which is held reduced by in the presence of succinate but oxidised in the presence of ATP (James, A. M., Smith, R. A. and Murphy, M. P. (2004) Arch. Biochem. Biophys. 423, 47-56; Ernster, L., Forsmark, P. and Nordenbrand, K. (1992) Biofactors 3, 241-8). In summary, all the Mitoquinone antioxidant compounds require activation by the respiratory chain to be effective antioxidants.

For FIG. 5A a single concentration of 5 pM was used for all the Mitoquinone antioxidant compounds. To compare their relative antioxidant efficacies we titrated the compounds in the presence of succinate: a typical titration is shown in FIG. 5C. This experiment suggests that the antioxidant efficacy of these compounds correlates with the length of the methylene bridge. To quantitate this we calculated the $IC_{50}$ values for the prevention of lipid peroxidation by the four exemplary Mitoquinone antioxidant compounds (FIG. 4D). These measurements confirmed that the order of antioxidant efficacy was: Mitoquinone-C15>Mitoquinone-C10>Mitoquinone-C5>Mitoquinone-C3.

All the Mitoquinone antioxidant compounds were accumulated into mitochondria driven by the mitochondrial membrane potential. For the most hydrophobic compound, Mitoquinone-C15, this effect was largely masked by extensive binding to phospholipid bilayers. All of the compounds were effective antioxidants and for persistent antioxidant activity over 15 minutes all required the action of the respiratory chain to recycle the Mitoquinone antioxidant compound to its active antioxidant form after having detoxified lipid peroxidation intermediates.

We believe, without wishing to be bound by any theory, that the range of membrane binding indicates that the compounds will have different locations within mitochondria, with the more hydrophobic compounds being substantially membrane adsorbed and the more hydrophilic compounds being substantially free in the matrix. This will allow the selective targeting of antioxidant activity to particular intracellular and/or intramitochondrial locations, for example, so as to target particular reactive oxygen species and/or particular sites of reactive oxygen species generation. We further believe the decreased non-specific binding of the less hydrophobic compounds will decrease the non-mitochondrial binding throughout the cell. This increased hydrophilicity of examples of antioxidant compounds will, for example, simplify their handling and may also lead to beneficial pharmacokinetic properties such as increased bioavailability.

Example 6

Effect of Mitochondrially Targeted Antioxidant Compounds on Cardiac Haemodynamics and Mitochondrial Function The effect of administration of mitochondrially targeted antioxidant compounds, in particular Mitoquinone-C10 and Mitoquinone-C3, on cardiac function was assessed using the Langendorf isolated heart perfusion model. Rats were assigned to the following four administration groups: Control (placebo), TPMP (methyltriphenyl phosphonium), Mitoquinone-C10, and Mitoquinone-C3. Following the treatment period, rats were humanely sacrificed and the isolated hearts were connected to the Langendorf isolated perfusion system. This system uses retro-perfusion through the aorta to maintain the heart while cardiac function is measured. Left ventricular pressure was measured with a left ventricular balloon. Coronary flow was also measured.

Figure 6:
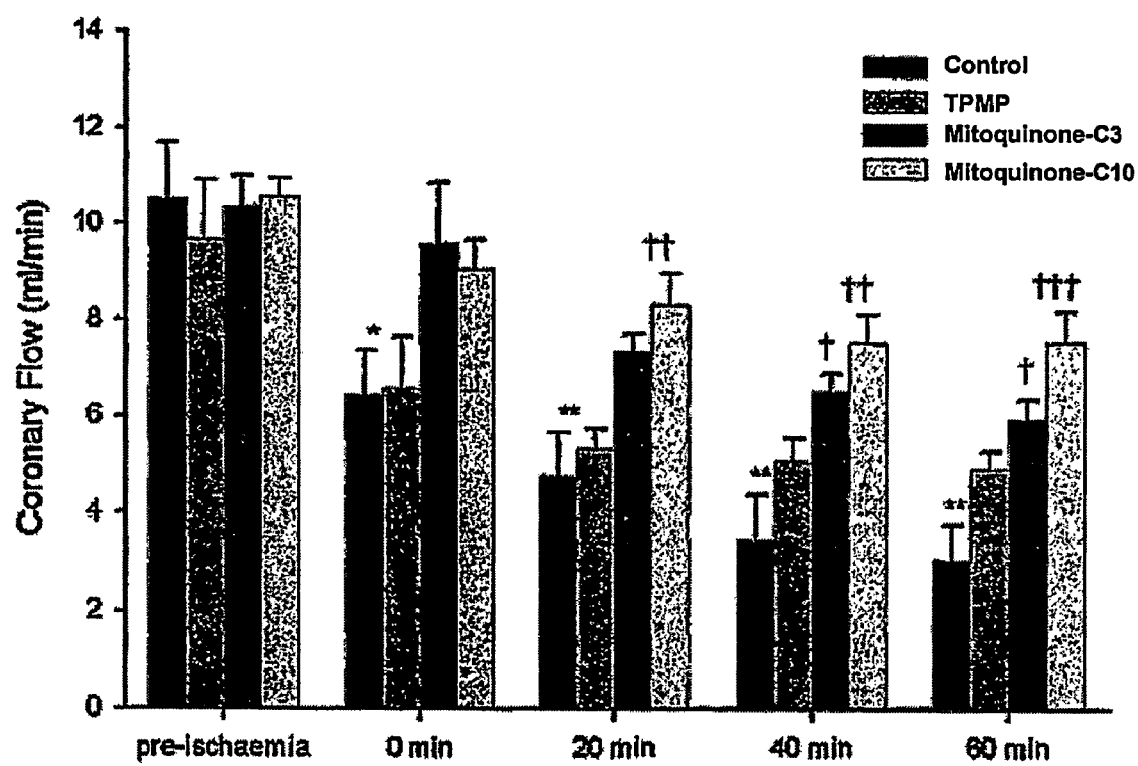
FIG. 6 presents a graph showing the effect of Mitoquinone-C10 and Mitoquinone-C3 on sinus coronary flow.

FIG. 6 depicts the coronary flow at 10 mmHg left ventricular pressure for each of the treatment groups. Coronary flow was measured pre-ischaemia and again at zero minutes, 20 minutes, 40 minutes and 60 minutes following induction of ischaemia. A one way ANOVA with bonferroni post hoc test was performed. Significance versus pre-ischaemic control: *$P<0.05$; $P<0.01$; * $P<0.001$. Significance versus respective time control: † $P<0.05$; †† $P<0.01$; ††† $P<0.001$.

The results show that treatment with Mitoquinone-C10 significantly reduces the ischaemia-induced reduction in coronary flow. Mitoquinone-C3 has a lesser but still significant effect at the later time points. The absence of any effect with administration of TPMP indicate that it is the antioxidant moiety of Mitoquinone-C10 and Mitoquinone-C3, and not the triphenylphosphonium cation, that is responsible for the effects observed with the mitochondrially targeted antioxidant compounds.

Figure 7:
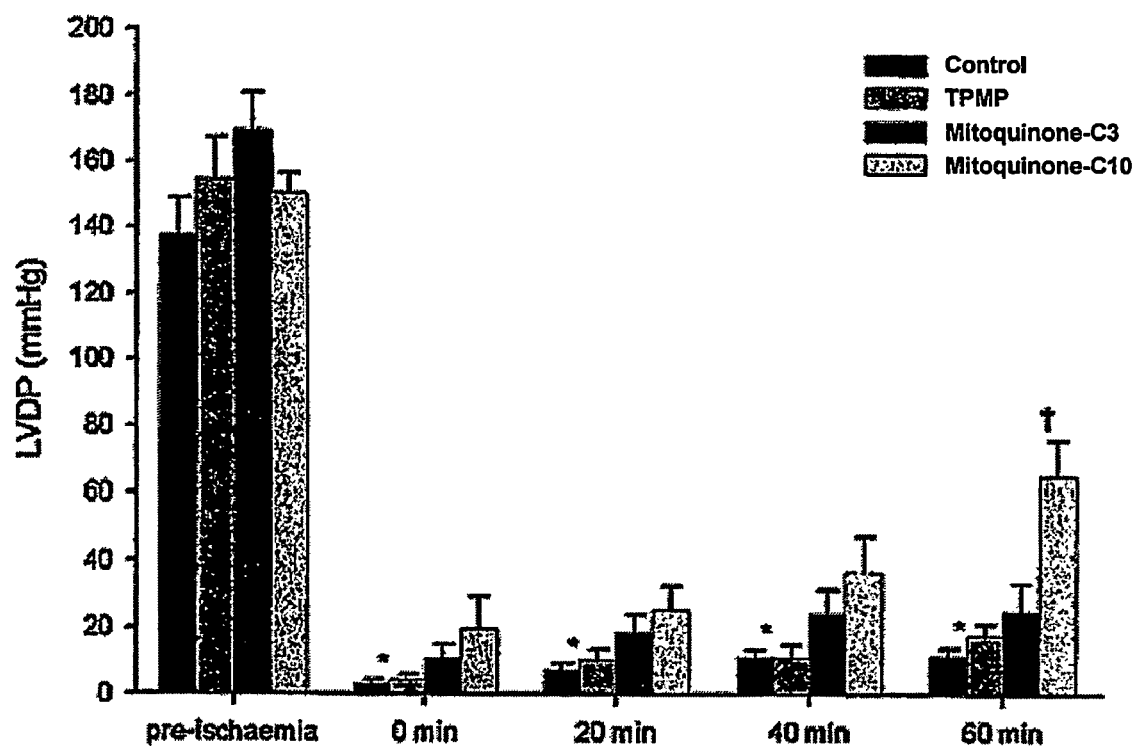
FIG. 7 presents a graph showing the effect of Mitoquinone-C10 and Mitoquinone-C3 on left ventricular diastolic pressure.

FIG. 7 depicts the effects of treatment on left ventricular diastolic pressure at 10 mmHg. Left ventricular diastolic pressure was measured prior to induction of ischaemia and again at zero minutes, 20 minutes, 40 minutes and 60 minutes following the induction of ischaemia. Statistical analysis was an ANOVA on ranks with Dunns post hoc test. Significance verses pre-ischaemic control: *$P<0.05$. † represents $P<0.05$ versus 60 min post ischaemic control. The results show that treatment with Mitoquinone-C10 results in a statistically significant increase in left ventricular diastolic pressure verses untreated rats, reducing the ischaemia-induced reduction in left ventricular diastolic pressure. The absence of any effect with administration of TPMP indicate that it is the antioxidant moiety of Mitoquinone-C10, and not the triphenylphosphonium cation, that is responsible for the effects observed with the mitochondrially targeted antioxidant compounds.

Figure 8:
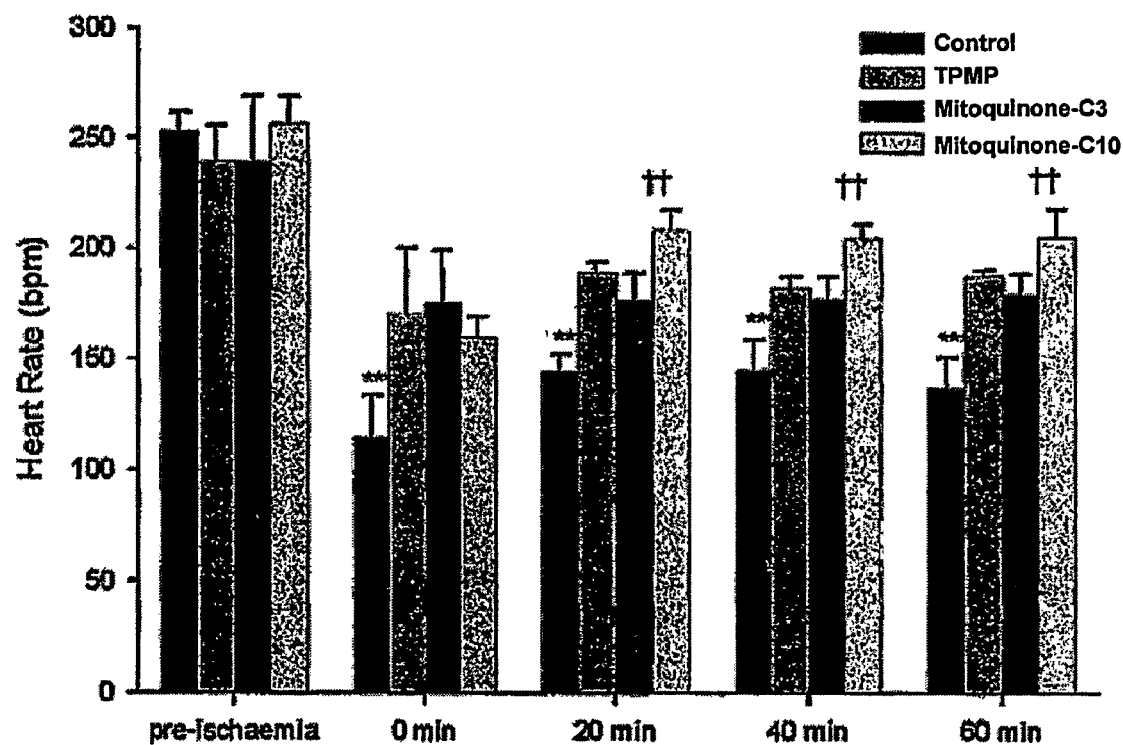
FIG. 8 present a graph which shows the effect of Mitoquinone-C10 and Mitoquinone-C3 on heart rate.

The effect of administration of Mitoquinone-C10 and Mitoquinone-C3 on heart rate was then determined. FIG. 8 depicts the heart rate for each of the treatment groups pre-ischaemia, and zero minutes, 20 minutes, 40 minutes and 60 minutes following the induction of ischaemia. Results shown are one way ANOVA followed by bonferroni post hoc test. *** represents $P<0.001$ versus pre-ischaemic control. †† represents $P<0.05$ versus respective post ischaemic control. The results show that treatment with Mitoquinone-C10 significantly reduces the ischaemia induced reduction in heart rate compared to control rats. The absence of any effect with administration of TPMP indicate that it is the antioxidant moiety of Mitoquinone-C10, and not the triphenylphosphonium cation, that is responsible for the effects observed with the mitochondrially targeted antioxidant compounds.

Figure 9:
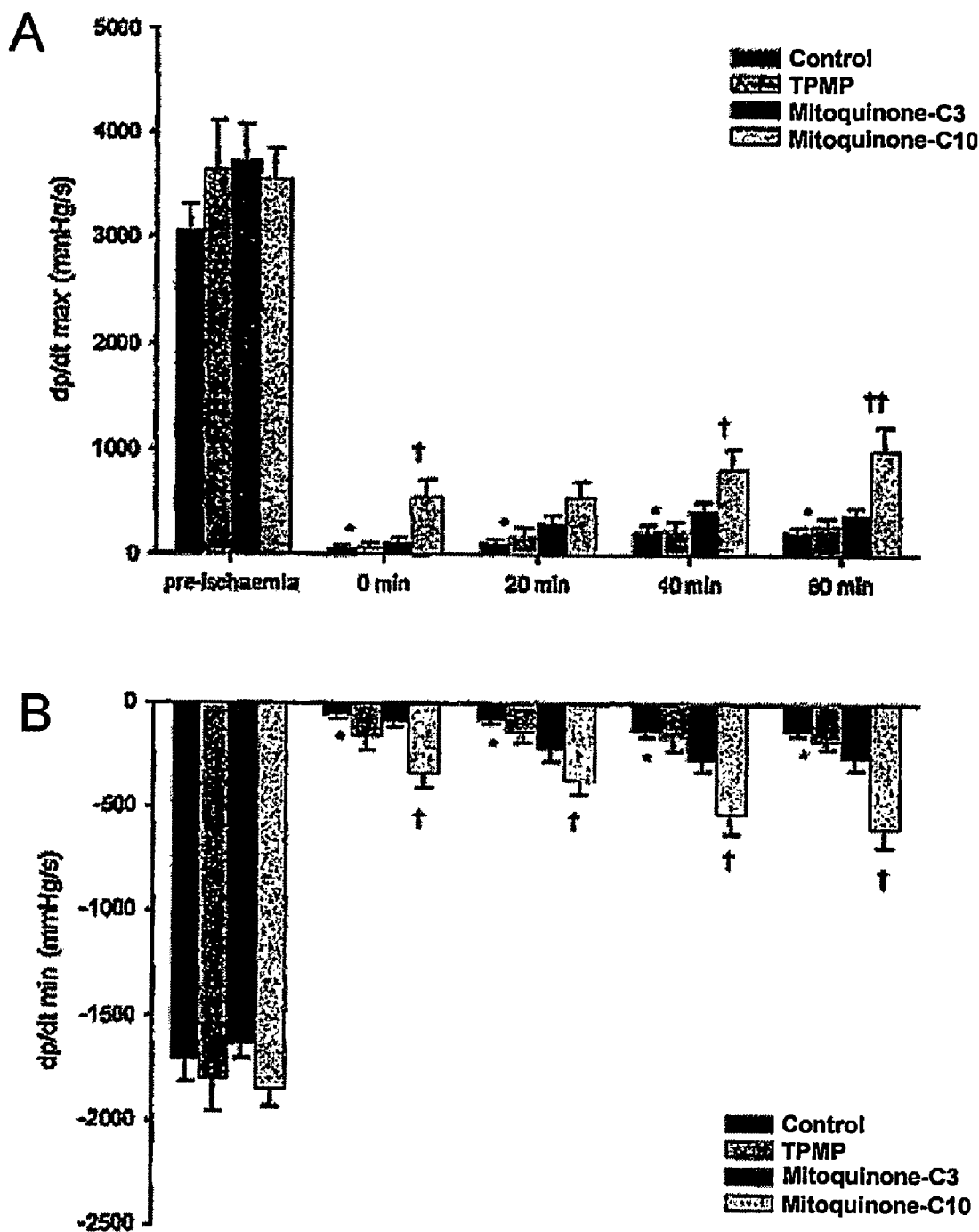
FIG. 9 presents graphs showing the rate of left ventricular change.

Cardiac function was further assessed by determining the effect of administration of mitochondrially targeted antioxidant compounds on the rate of contraction and relaxation of the heart. FIG. 9A depicts the rate of contraction in each of the four treatment groups pre-ischaemia, and zero minutes, 20 minutes, 40 minutes and 60 minutes following induction of ischaemia. FIG. 9B depicts the rate of relaxation in each of the four treatment groups pre-ischaemia, and zero minutes, 20 minutes, 40 minutes and 60 minutes following induction of ischaemia. In each case ANOVA was performed on ranks with Dunns post hoc test performed. * represents significance with $P<0.05$ verses pre-ischaemia control. † represents significance with $P<0.05$ versus respective post ischaemic time controls. †† represents significance with $P<0.01$ versus respective post ischaemic time control.

The results show that administration of Mitoquinone-C10 has a statistically significant effect, reducing the ischaemia-induced reduction in the rate of contraction and relaxation of the left ventricle when compared to control rats.

Figure 10:
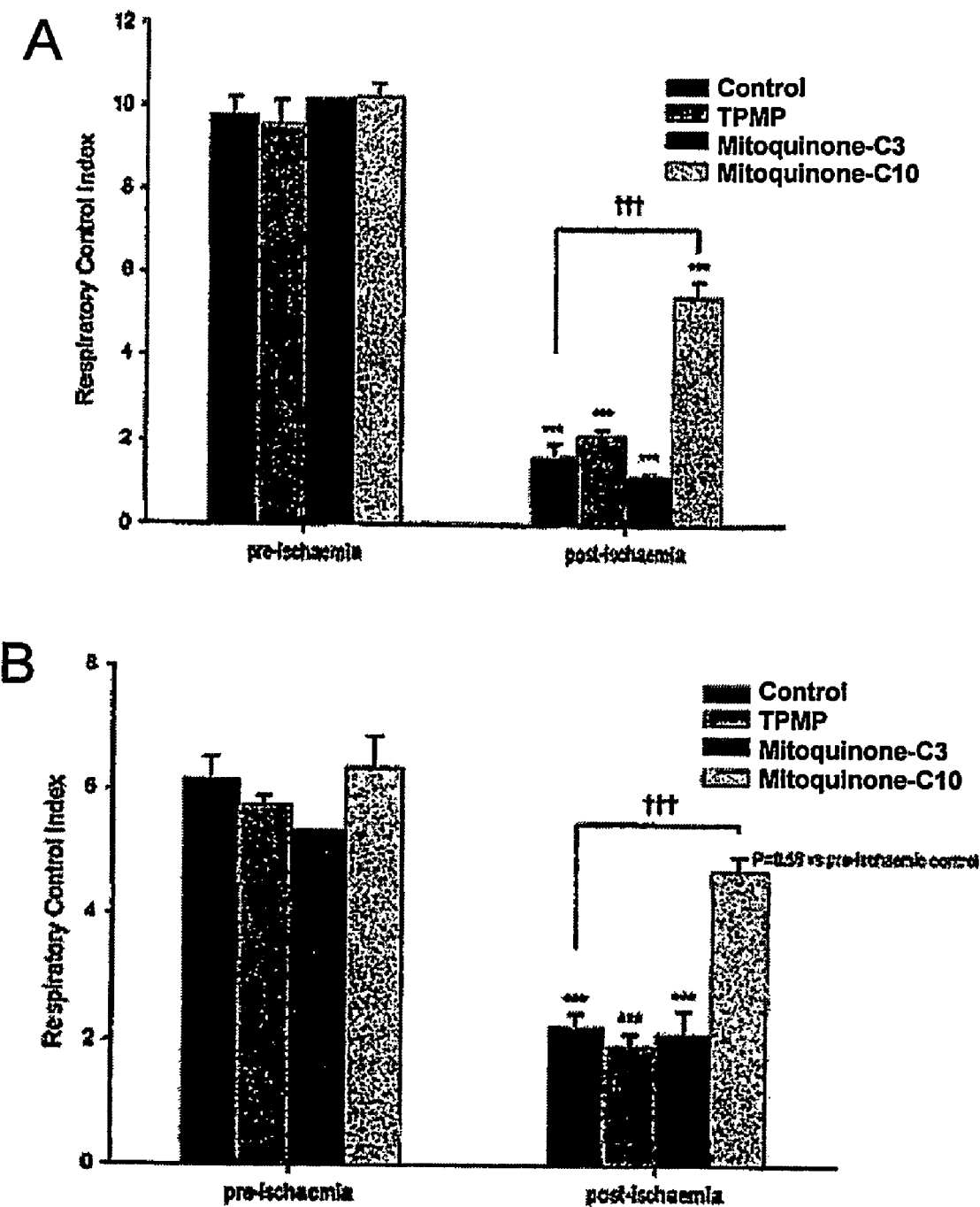
FIG. 10 depicts graphs showing the effect of Mitoquinone-C10 and Mitoquinone-C3 on post ischaemia mitochondrial respiratory function.

The above data clearly show the beneficial effect of administration of mitochondrially targeted antioxidant compounds on cardiac function. In order to determine whether the observed effects on cardiac function were due to the effect of the mitochondrial targeted antioxidant compound on mitochondrial function, mitochondrial activity pre-ischaemia and post-ischaemia was assessed for each of the treatment groups. FIG. 10A depicts NAD$^+$ linked respiratory function of mitochondria pre and post-ischaemia for each of the four treatment groups. FIG. 10B presents FAD linked respiratory function pre and post-ischaemia for each of the four treatment groups. *** represents significance with $P<0.001$ versus pre-ischaemic control. ††† represents significance with $P<0.001$ versus post ischaemic control.

These data show that Mitoquinone-C10 has a statistically significant beneficial effect on mitochondrially respiratory function following ischaemia compared to control rats. These results support the conclusion that the effects of administration of mitochondrially targeted antioxidant compounds on cardiac function is due to a protective effect on mitochondrial function.

All patents, publications, scientific articles, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of various embodiments or preferred embodiments and are exemplary only and not intended as limitations on the scope of the invention. Other objects, aspects, examples and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", "containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

The compounds of the invention have application in selective antioxidant therapies for human patients to prevent mitochondrial damage. This can be to prevent the elevated mitochondrial oxidative stress associated with particular diseases, such as Parkinson's disease or diseases associated with mitochondrial DNA mutations. They could also be used in conjunction with cell transplant therapies for neurodegenerative diseases, to increase the survival rate of implanted cells.

In addition, these compounds could be used as prophylactics to protect organs during transplantation, or ameliorate the ischaemia-reperfusion injury that occurs during surgery. The compounds of the invention could also be used to reduce cell damage following stroke and heart attack or be given prophylactically to premature babies, which are susceptible to brain ischemia. The methods of the invention have a major advantage over current antioxidant therapies—they will enable antioxidants to accumulate selectively in mitochondria, the part of the cell under greatest oxidative stress. This will greatly increase the efficacy of antioxidant therapies.

Those persons skilled in the art will appreciate that the above description is provided by way of example only, and that different lipophilic cation/antioxidant combinations can be employed without departing from the scope of the invention.

The invention claimed is:

1. A mitochondrially targeted antioxidant compound, comprising:
    a lipophilic cationic moiety linked by a linking moiety to an antioxidant moiety; and
    a salt forming anion that is not a bromide anion or a nitrate anion and does not exhibit reactivity against the lipophilic cationic moiety, the linking moiety or the antioxidant moiety, wherein the antioxidant compound accumulates within mitochondria of an intact cell, and wherein at least one of the linking moiety, the lipophilic cationic moiety and the antioxidant moiety is selected such that within mitochondria the antioxidant moiety resides at a desired location within said mitochondria.

2. The compound of claim 1 wherein the desired location is selected from the group consisting of an outer mitochondrial membrane, a mitochondrial intermembrane space, an inner mitochondrial membrane and a mitochondrial matrix.

3. A mitochondrially targeted antioxidant compound, comprising:
    a lipophilic cationic moiety linked by a linking moiety to an antioxidant moiety; and
    a salt forming anion that is not a bromide anion or a nitrate anion and does not exhibit reactivity against the lipophilic cationic moiety, the linking moiety or the antioxidant moiety, wherein the antioxidant compound accumulates within mitochondria of an intact cell, and wherein within said mitochondria the antioxidant moiety is at a distance from the lipophilic cationic moiety of between about 5 Angstroms and about 60 Angstroms.

4. The compound of claim 3 wherein the antioxidant moiety is at a distance from the lipophilic cationic moiety that is selected from the group consisting of (i) a distance of between about 10 angstroms and about 50 angstroms, (ii) a distance of between about 20 angstroms and about 40 angstroms, and (iii) a distance of between about 25 angstroms and about 35 angstroms.

5. The compound of claim 3 wherein the linking moiety is selected from the group consisting of (i) a carbon chain having from about 1 to about 30 carbon atoms, (ii) a carbon chain having from about 2 to about 20 carbon atoms, (iii) a carbon chain having from about 2 to about 15 carbon atoms, (iv) a carbon chain having from about 3 to about 10 carbon atoms, and (v) a carbon chain having from about 3 to about 6 carbon atoms.

6. A compound according to claim 3 which comprises at least one formula selected from the group consisting of:

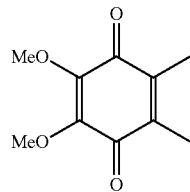 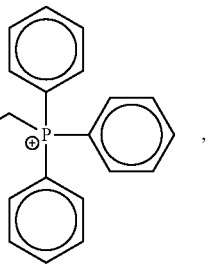

I

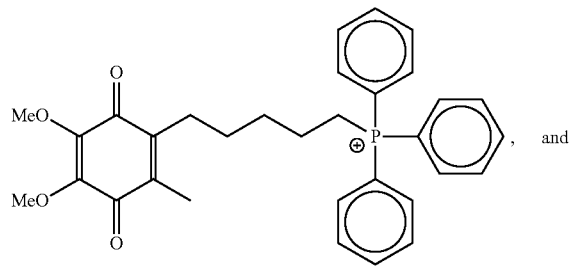, and 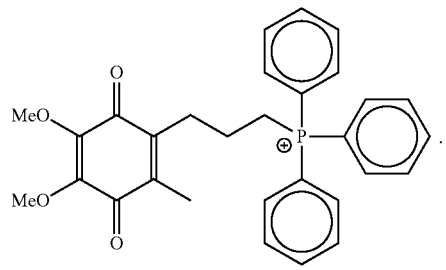

II                III

7. A mitochondrially targeted antioxidant compound, comprising:
a lipophilic cationic moiety linked by a linking moiety to an antioxidant moiety; and
a salt forming anion that is not a bromide anion or a nitrate anion and does not exhibit reactivity against the lipophilic cationic moiety, the linking moiety or the antioxidant moiety, wherein the antioxidant compound has a partition coefficient of less than about 20 in octanol:water and accumulates within mitochondria of an intact cell.

8. The antioxidant compound of any one of claims 1, 3 and 7 wherein the lipophilic cationic moiety comprises a cation that is selected from the group consisting of a triphenylphosphonium cation, a tribenzylammonium cation and a phosphonium cation.

9. The antioxidant compound of any one of claims 1, 3 and 7 wherein the salt forming anion comprises an alkyl sulfonate or an aryl sulfonate.

10. The antioxidant compound of claim 9 wherein the alkyl sulfonate or aryl sulfonate is selected from the group consisting of methanesulfonate, ethanesulfonate, propanesulfonate, benzene sulfonate, p-toluene sulfonate and 2-napthylene sulfonate.

11. The antioxidant compound of any one of claims 1, 3 and 7 wherein the salt forming anion comprises methanesulfonate.

12. The antioxidant compound of any one of claims 1, 3 and 7 wherein the salt forming anion comprises a non-nucleophilic anion that is selected from the group consisting of hexafluoroantimonate, hexafluoroarsenate, hexafluorophosphate, tetraphenylborate, tetra(perfluorophenyl)borate and trifluoromethane sulfonate.

13. The antioxidant compound of any one of claims 1, 3 and 7 wherein the antioxidant moiety comprises a quinone or a quinol.

14. The antioxidant compound of any one of claims 1, 3 and 7 wherein the antioxidant moiety is capable of interacting with a mitochondrial reductant to obtain or regain antioxidant activity.

15. The antioxidant compound of claim 14 wherein the mitochondrial reductant comprises mitochondrial Complex II.

16. A pharmaceutical composition comprising an antioxidant compound according to any one of claims 1, 3 and 7; and a carrier or excipient.

17. The pharmaceutical composition according to claim 16 wherein the antioxidant compound comprises a compound which comprises a formula that is selected from the group consisting of:

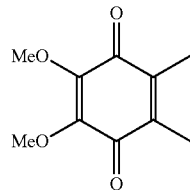

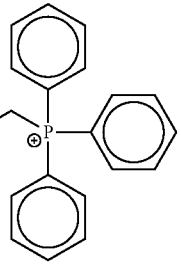

I

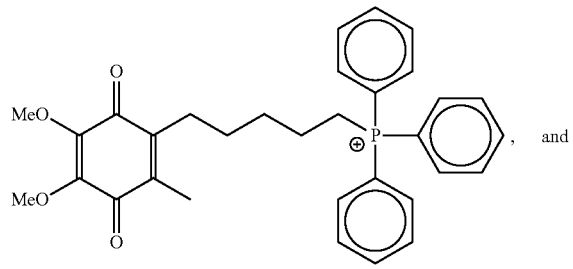

II

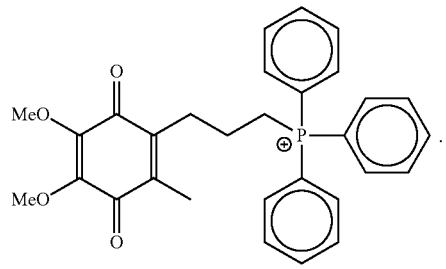

III

18. An antioxidant compound according to claim 7 which comprises a structure of the following formula:

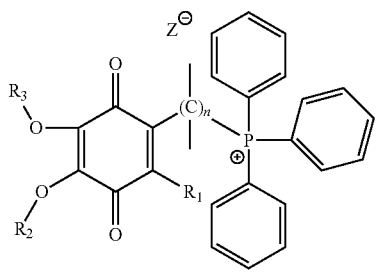

or its quinol form, wherein $R_1$, $R_2$, and $R_3$, are the same or different and are selected from $C_1$ to $C_5$ alkyl, substituted $C_1$ to $C_5$ alkyl and H, and wherein n is an integer from 2 to 20, and wherein Z is the salt forming anion.

19. A pharmaceutical composition comprising an antioxidant compound according to claim 16 and a carrier or excipient.

20. The pharmaceutical composition according to claim 16 which comprises cyclodextrin.

21. The pharmaceutical composition of claim 20 wherein the antioxidant compound and cyclodextrin are present at a compound-to-cyclodextrin molar ratio that is from about 10:1 to about 1:10.

22. The pharmaceutical composition of claim 20 wherein the antioxidant compound and cyclodextrin are present at a compound-to-cyclodextrin molar ratio that is selected from the group consisting of (i) from about 5:1 to about 1:5, (ii) from about 4:1 to about 1:4, (iii) from about 2:1 to about 1:2, (iv) about 1:1 and (v) about 1:2.

23. A method of reducing oxidative stress in a cell, comprising:
    contacting a cell that comprises mitochondria with an antioxidant compound that comprises an antioxidant compound according to claim 18.

24. A method of reducing oxidative stress in a cell, comprising:
    contacting a cell that comprises mitochondria with an antioxidant compound that comprises at least one antioxidant compound that is selected from the group consisting of an antioxidant compound according to claim 1, an antioxidant compound according to claim 3, and an antioxidant compound according to claim 7.

25. A method of therapy of a patient who would benefit from reduced oxidative stress, comprising administering to said patient a therapeutically efficacious dose of a pharmaceutical composition which comprises (i) an antioxidant compound that comprises at least one antioxidant compound that is selected from the group consisting of an antioxidant compound according to claim 1, an antioxidant compound according to claim 3, and an antioxidant compound according to claim 7, and (ii) a carrier or excipient.

26. A method of screening for a mitochondrially localizing amphiphilic antioxidant compound, comprising:
    (a) administering a candidate amphiphilic antioxidant compound to a mitochondrial preparation comprising deenergized mitochondria, to determine binding of the compound to mitochondria that substantially lack a mitochondrial membrane potential;
    (b) energizing the mitochondria of (a) to determine mitochondrial uptake of the candidate amphiphilic antioxidant compound in the presence of a mitochondrial membrane potential;
    (c) deenergizing the mitochondria to abolish the membrane potential; and
    (d) determining mitochondrial release of the candidate amphiphilic antioxidant compound in the absence of the mitochondrial membrane potential, wherein incomplete release of said compound indicates mitochondrial localization.

27. A method for synthesizing a compound of the formula I

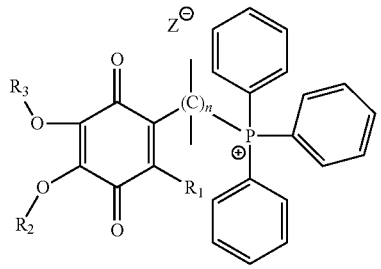

or its quinol form, wherein $R_1$, $R_2$, and $R_3$, are the same or different and are selected from $C_1$ to $C_5$ alkyl, substituted $C_1$ to $C_5$ alkyl and H, and wherein n is an integer from 2 to 20, and wherein Z is a salt forming anion that is not a bromide anion or a nitrate anion and does not exhibit reactivity against the compound, the method comprising formation of the compound from triphenylphosphonium without a reaction solvent.

28. The method of claim 27 wherein each C of (C)n is saturated.

29. The method of claim 27 wherein the compound has a partition coefficient in octanol:water of less than about 20.

30. A method for synthesizing an antioxidant compound of the formula I

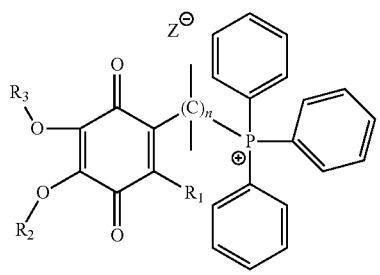

or its quinol form, wherein $R_1$, $R_2$, and $R_3$, are the same or different and are selected from $C_1$ to $C_5$ alkyl, substituted $C_1$ to $C_5$ alkyl and H, and wherein n is an integer from 2 to 20, and wherein Z is a salt forming anion that is not a bromide anion or a nitrate anion and does not exhibit reactivity against the compound, the method comprising a reaction of a reactant compound of the formula IV

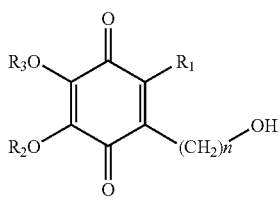

or its quinol form in the presence of $Ph_3PHX$ and $Ph_3P$, where X is a halogen atom.

31. The method of claim 30 wherein the halogen is selected from the group consisting of bromine, iodine and chlorine.

32. The method of claim 30 wherein the halogen is bromine.

33. The method of claim 30 wherein n is an integer that is selected from the group consisting of 2, 3, 4 and 5.

34. The method of claim 30 wherein the reaction is maintained at a temperature below which significant amounts of $R_2PPh_3$ or $R_3PPh_3$ are not formed by ether cleavage.

35. The method of claim 30 wherein the reaction is kept below 80° C.

36. The method of claim 30 which comprises the reaction, without a reaction solvent.

37. A method for synthesizing an antioxidant compound of the formula (2)

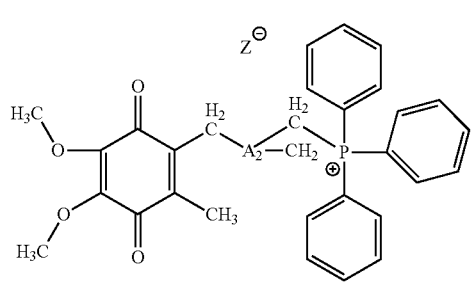

or its quinol form, wherein Z is a salt forming anion that is not a bromide anion or a nitrate anion and does not exhibit reactivity against the compound, the method comprising a reaction of a reactant compound of the formula (3)

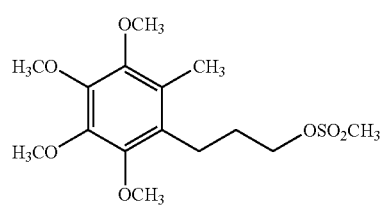

in the presence of $Ph_3P$ and X, where X comprises a halogen atom.

38. The method of claim 37 wherein the halogen is selected from the group consisting of bromine, iodine and chlorine.

39. The method of claim 37 wherein the halogen is bromine.

40. The method of claim 37 which comprises formation of the antioxidant compound from triphenylphosphonium without a reaction solvent.

* * * * *

UNITED STATES PATENT AND TRADEMARK OFFICE
CERTIFICATE OF CORRECTION

| | | |
|---|---|---|
| PATENT NO. | : 7,888,334 B2 | Page 1 of 1 |
| APPLICATION NO. | : 10/568654 | |
| DATED | : February 15, 2011 | |
| INVENTOR(S) | : Michael Patrick Murphy et al. | |

It is certified that error appears in the above-identified patent and that said Letters Patent is hereby corrected as shown below:

Column 49, Lines 48-49:
"an antioxidant compound according to claim 16 and a carrier or" should read, --an antioxidant compound according to claim 18; and a carrier or--.

Signed and Sealed this
Twenty-seventh Day of September, 2011

David J. Kappos
*Director of the United States Patent and Trademark Office*